(12) United States Patent
Felton et al.

(10) Patent No.: US 12,314,632 B2
(45) Date of Patent: May 27, 2025

(54) METHODS AND USER INTERFACES FOR MONITORING SOUND REDUCTION

(71) Applicant: Apple Inc., Cupertino, CA (US)

(72) Inventors: Nicholas D. Felton, Sunnyvale, CA (US); Ruchi N. Goswami, Sunnyvale, CA (US); Matthew E. Leon, San Francisco, CA (US); David Harrison, Mountain View, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/648,790

(22) Filed: Apr. 29, 2024

(65) Prior Publication Data

US 2024/0281204 A1  Aug. 22, 2024

Related U.S. Application Data

(63) Continuation of application No. 18/195,331, filed on May 9, 2023, now Pat. No. 12,008,290.

(60) Provisional application No. 63/342,623, filed on May 16, 2022.

(51) Int. Cl.
  *G06F 3/0484* (2022.01)
  *G06F 3/0482* (2013.01)
  *G06F 3/16* (2006.01)
  *H04R 29/00* (2006.01)

(52) U.S. Cl.
  CPC ............ *G06F 3/165* (2013.01); *G06F 3/0482* (2013.01); *G06F 3/0484* (2013.01); *H04R 29/008* (2013.01)

(58) Field of Classification Search
  CPC .............................................. G06F 3/048–05
  See application file for complete search history.

(56) References Cited

U.S. PATENT DOCUMENTS

| | | | |
|---|---|---|---|
| 6,873,709 B2 | 3/2005 | Hou | |
| 8,045,739 B2 | 10/2011 | Paludan-Mueller et al. | |
| 9,489,809 B1* | 11/2016 | Dever | A61B 5/6803 |
| 9,490,763 B2 | 11/2016 | Taniguchi et al. | |
| 10,024,711 B1* | 7/2018 | Sanchez | A61B 5/7455 |

(Continued)

FOREIGN PATENT DOCUMENTS

| | | |
|---|---|---|
| CN | 103474080 A | 12/2013 |
| CN | 103927175 A | 7/2014 |

(Continued)

OTHER PUBLICATIONS

Applicant-Initiated Interview Summary received for U.S. Appl. No. 17/554,678, mailed on Apr. 23, 2024, 4 pages.

(Continued)

*Primary Examiner* — Daniel Rodriguez
(74) *Attorney, Agent, or Firm* — DLA Piper LLP (US)

(57) ABSTRACT

The present disclosure generally relates to user interfaces and techniques for managing and visualizing sound reduction using a computer system. In accordance with some embodiments, the computer system displays a representation of a noise level including, in accordance with a sound reduction display option being enabled, a first indication of a noise level at a first time and a second indication of a noise level at a time different from the first time. In accordance with some embodiments, in accordance with a determination that the sound reduction display option is not enabled, an indication of a noise level at the first time that indicates the noise level.

42 Claims, 21 Drawing Sheets

(56) References Cited

U.S. PATENT DOCUMENTS

| | | | |
|---|---|---|---|
| 10,068,451 B1* | 9/2018 | Werner | H04R 29/00 |
| 10,764,700 B1 | 9/2020 | Felton | |
| 2003/0191609 A1 | 10/2003 | Bernardi et al. | |
| 2004/0190729 A1* | 9/2004 | Yonovitz | G01H 3/14 |
| | | | 381/72 |
| 2005/0244013 A1 | 11/2005 | Battenberg et al. | |
| 2006/0182287 A1 | 8/2006 | Schulein et al. | |
| 2006/0210096 A1 | 9/2006 | Stokes et al. | |
| 2006/0274908 A1 | 12/2006 | Choi | |
| 2007/0274531 A1 | 11/2007 | Camp | |
| 2008/0159547 A1 | 7/2008 | Schuler et al. | |
| 2008/0205660 A1 | 8/2008 | Goldstein | |
| 2009/0007596 A1 | 1/2009 | Goldstein et al. | |
| 2009/0052677 A1 | 2/2009 | Smith | |
| 2009/0180631 A1 | 7/2009 | Michael et al. | |
| 2009/0245537 A1 | 10/2009 | Morin | |
| 2009/0287327 A1 | 11/2009 | Hsu et al. | |
| 2009/0290721 A1 | 11/2009 | Goldstein et al. | |
| 2010/0014682 A1* | 1/2010 | Shin | H03G 3/3026 |
| | | | 381/57 |
| 2010/0027807 A1 | 2/2010 | Jeon | |
| 2010/0046767 A1 | 2/2010 | Bayley et al. | |
| 2010/0119093 A1 | 5/2010 | Uzvanis et al. | |
| 2010/0150378 A1 | 6/2010 | Lee et al. | |
| 2012/0033827 A1* | 2/2012 | Murata | H04R 3/002 |
| | | | 381/94.1 |
| 2012/0051555 A1 | 3/2012 | Schevciw et al. | |
| 2012/0321094 A1 | 12/2012 | Schiller et al. | |
| 2013/0002425 A1* | 1/2013 | Hatch | G01H 3/12 |
| | | | 345/633 |
| 2013/0073933 A1 | 3/2013 | Eppolito | |
| 2013/0073960 A1 | 3/2013 | Eppolito et al. | |
| 2013/0202121 A1 | 8/2013 | Georgiou et al. | |
| 2014/0037107 A1 | 2/2014 | Marino et al. | |
| 2014/0189510 A1 | 7/2014 | Ozcan | |
| 2014/0267543 A1* | 9/2014 | Kerger | G06F 3/04883 |
| | | | 348/14.02 |
| 2014/0275856 A1 | 9/2014 | Kohlrausch et al. | |
| 2014/0327527 A1 | 11/2014 | Goldstein et al. | |
| 2015/0032451 A1* | 1/2015 | Gunn | G10L 15/20 |
| | | | 704/244 |
| 2015/0110277 A1 | 4/2015 | Pidgeon et al. | |
| 2015/0110279 A1 | 4/2015 | Tejerina | |
| 2015/0179186 A1 | 6/2015 | Swierk et al. | |
| 2015/0287421 A1 | 10/2015 | Benway et al. | |
| 2015/0350799 A1 | 12/2015 | Schnaare et al. | |
| 2016/0080537 A1 | 3/2016 | Kim | |
| 2016/0119709 A1* | 4/2016 | Beurton | H03G 5/165 |
| | | | 381/74 |
| 2017/0011600 A1* | 1/2017 | Joung | H04M 1/72442 |
| 2017/0070833 A1 | 3/2017 | Shennib | |
| 2017/0230788 A1* | 8/2017 | Simonides | H04R 25/505 |
| 2017/0357329 A1 | 12/2017 | Park et al. | |
| 2018/0014121 A1 | 1/2018 | Lawrence et al. | |
| 2018/0039410 A1 | 2/2018 | Kim et al. | |
| 2019/0073618 A1 | 3/2019 | Kanukurthy et al. | |
| 2019/0278556 A1 | 9/2019 | Usher et al. | |
| 2019/0313180 A1 | 10/2019 | Kadiwala et al. | |
| 2020/0382866 A1 | 12/2020 | Felton | |
| 2020/0382867 A1* | 12/2020 | Felton | G06F 3/04847 |
| 2020/0382868 A1* | 12/2020 | Felton | H04R 29/008 |
| 2022/0109932 A1 | 4/2022 | Felton et al. | |
| 2022/0286797 A1* | 9/2022 | Wilson | G01H 7/00 |
| 2023/0367542 A1 | 11/2023 | Felton et al. | |

FOREIGN PATENT DOCUMENTS

| | | | |
|---|---|---|---|
| CN | 103986813 A | 8/2014 | |
| CN | 105632508 A | 6/2016 | |
| CN | 107508995 A | 12/2017 | |
| CN | 109287140 A | 1/2019 | |
| EP | 2391004 A1 | 11/2011 | |
| EP | 3255897 A1 | 12/2017 | |
| JP | 2004-80496 A | 3/2004 | |
| JP | 2007-88521 A | 4/2007 | |
| JP | 2009-44365 A | 2/2009 | |
| JP | 2009-232301 A | 10/2009 | |
| JP | 2009-538571 A | 11/2009 | |
| JP | 2012-244522 A | 12/2012 | |
| JP | 2013-207323 A | 10/2013 | |
| JP | 2017-526073 A | 9/2017 | |
| JP | 2018-191122 A | 11/2018 | |
| KR | 10-2002-0060421 A | 7/2002 | |
| KR | 10-2008-0051460 A | 6/2008 | |
| KR | 10-2009-0010287 A | 1/2009 | |
| KR | 10-2015-0115385 A | 10/2015 | |
| KR | 10-2018-0018761 A | 2/2018 | |
| WO | 03/067202 A2 | 8/2003 | |
| WO | 2015/009430 A2 | 1/2015 | |
| WO | 2016/036472 A1 | 3/2016 | |
| WO | 2017/215203 A1 | 12/2017 | |
| WO | 2018/148356 A1 | 8/2018 | |
| WO | 2018/213401 A1 | 11/2018 | |
| WO | 2020/247289 A1 | 12/2020 | |

OTHER PUBLICATIONS

Intention to Grant received for European Patent Application No. 20746438.9, mailed on Mar. 21, 2024, 15 pages.

Decision to Grant received for European Patent Application No. 20746438.9, mailed on Aug. 22, 2024, 4 pages.

Notice of Allowance received for Korean Patent Application No. 10-2022-7012608, mailed on Aug. 22, 2024, 9 pages (2 pages of English Translation and 7 pages of Official Copy).

Notice of Allowance received for U.S. Appl. No. 17/554,678, mailed on Jul. 9, 2024, 7 pages.

Corrected Notice of Allowance received for U.S. Appl. No. 17/554,678, mailed on Sep. 18, 2024, 2 pages.

Applicant-Initiated Interview Summary received for U.S. Appl. No. 16/584,186, mailed on Feb. 3, 2020, 4 pages.

Applicant-Initiated Interview Summary received for U.S. Appl. No. 16/880,552, mailed on Apr. 21, 2021, 3 pages.

Applicant-Initiated Interview Summary received for U.S. Appl. No. 16/880,552, mailed on Dec. 16, 2020, 6 pages.

Applicant-Initiated Interview Summary received for U.S. Appl. No. 16/880,552, mailed on Oct. 20, 2020, 6 pages.

Applicant-Initiated Interview Summary received for U.S. Appl. No. 16/907,261, mailed on Dec. 16, 2020, 6 pages.

Applicant-Initiated Interview Summary received for U.S. Appl. No. 16/907,261, mailed on Jul. 16, 2021, 10 pages.

Applicant-Initiated Interview Summary received for U.S. Appl. No. 16/907,261, mailed on Mar. 25, 2021, 2 pages.

Brief Communication Regarding Oral Proceedings received for European Patent Application No. 20746438.9, mailed on Nov. 7, 2022, 1 page.

Casella Cel Casella, "The Casella dBadge2—World's First Truly Wireless Noise Dosimeter and Airwave App!", Retrieved from URL: <https://www.youtube.com/watch?v=Xvy2fl3cgYo>, May 27, 2015, 3 pages.

Corrected Notice of Allowance received for U.S. Appl. No. 16/584,186, mailed on Jul. 31, 2020, 2 pages.

Corrected Notice of Allowance received for U.S. Appl. No. 16/880,552, mailed on Dec. 22, 2021, 2 pages.

Corrected Notice of Allowance received for U.S. Appl. No. 16/880,552, mailed on Dec. 23, 2020, 2 pages.

Corrected Notice of Allowance received for U.S. Appl. No. 16/880,552, mailed on Jul. 7, 2021, 2 pages.

Corrected Notice of Allowance received for U.S. Appl. No. 16/921,312, mailed on Dec. 7, 2021, 2 pages.

Corrected Notice of Allowance received for U.S. Appl. No. 16/921,312, mailed on Sep. 24, 2021, 2 pages.

Creating Charts in SQL Developer 4.0, Online available at: https://web.archive.org/web/20130905014633/https://www.oracle.com/webfolder/technetwork/tutorials/obe/db/sqldev/r40/Chart/12cChart.html, Sep. 5, 2013, 6 pages.

Final Office Action received for U.S. Appl. No. 16/907,261, mailed on Mar. 18, 2021, 20 pages.

(56) References Cited

OTHER PUBLICATIONS

Gertz Michael, "Oracle/SQL Tutorial", Online available at: http://www.db.cs.ucdavis.edu/teaching/sqltutorial/tutorial.pdf, Jan. 1, 2000, 5 pages.
Gupta Rajat, "Disable High vol. Warning (no root) in Samsung S7, S8 / Android 7.0", Online available at: <https://www.youtube.com/watch?v=9fKwRBtk-x8>, Retrieved on Nov. 26, 2020; esp. 2:04, Aug. 6, 2017, 1 page.
International Preliminary Report on Patentability received for PCT Patent Application No. PCT/US2020/025768, mailed on Dec. 16, 2021, 8 pages.
International Preliminary Report on Patentability received for PCT Patent Application No. PCT/US2020/035474, mailed on Dec. 16, 2021, 11 pages.
International Search Report and written Opinion received for PCT Patent Application No. PCT/US2020/025768, mailed on Aug. 10, 2020, 11 pages.
International Search Report and Written Opinion received for PCT Patent Application No. PCT/US2020/035474, mailed on Nov. 26, 2020, 16 pages.
International Search Report and Written Opinion received for PCT Patent Application No. PCT/US2023/021923, mailed on Oct. 4, 2023, 38 pages.
Invitation to Pay Addition Fees received for PCT Patent Application No. PCT/US2020/035474, mailed on Oct. 2, 2020, 11 pages.
Invitation to Pay Additional Fee received for PCT Patent Application No. PCT/US2023/021923, mailed on Aug. 25, 2023, 18 pages.
Invitation to Pay Search Fees received for European Patent Application No. 20746438.9, mailed on Dec. 2, 2022, 4 pages.
Megadepot, "Casella dBadge2 Noise Dosimeter", Retrieved from URL: <https://www.youtube.com/watch?v=pHIHLiYCD08>, Jun. 12, 2018, 3 pages.
Non-Final Office Action received for U.S. Appl. No. 16/584,186, mailed on Dec. 6, 2019, 13 pages.
Non-Final Office Action received for U.S. Appl. No. 16/880,552, mailed on Feb. 19, 2021, 11 pages.
Non-Final Office Action received for U.S. Appl. No. 16/880,552, mailed on Jul. 23, 2020, 19 pages.
Non-Final Office Action received for U.S. Appl. No. 16/907,261, mailed on Sep. 30, 2020, 22 pages.
Non-Final Office Action received for U.S. Appl. No. 17/554,678, mailed on Feb. 1, 2024, 10 pages.
Non-Final Office Action received for U.S. Appl. No. 18/195,331, mailed on Feb. 8, 2024, 13 pages.
Notice of Acceptance received for Australian Patent Application No. 2020288147, mailed on Dec. 22, 2021, 3 pages.
Notice of Acceptance received for Australian Patent Application No. 2022202459, mailed on May 11, 2023, 3 pages.
Notice of Acceptance received for Australian Patent Application No. 2023212604, mailed on Oct. 12, 2023, 3 pages.
Notice of Allowance received for Japanese Patent Application No. 2021-571467, mailed on Apr. 11, 2022, 4 pages.
Notice of Allowance received for Japanese Patent Application No. 2022-078277, mailed on Oct. 27, 2023, 4 pages.
Notice of Allowance received for Korean Patent Application No. 10-2021-7042504, mailed on Jan. 17, 2022, 6 pages.
Notice of Allowance received for U.S. Appl. No. 16/584,186, mailed on Mar. 24, 2020, 10 pages.
Notice of Allowance received for U.S. Appl. No. 16/880,552, mailed on Dec. 1, 2020, 7 pages.
Notice of Allowance received for U.S. Appl. No. 16/880,552, mailed on Jul. 23, 2021, 5 pages.
Notice of Allowance received for U.S. Appl. No. 16/880,552, mailed on May 12, 2021, 7 pages.
Notice of Allowance received for U.S. Appl. No. 16/880,552, mailed on Nov. 24, 2021, 5 pages.
Notice of Allowance received for U.S. Appl. No. 16/907,261, mailed on Aug. 13, 2021, 8 pages.
Notice of Allowance received for U.S. Appl. No. 18/195,331, mailed on Sep. 28, 2021, 6 pages.
Notice of Allowance received for U.S. Appl. No. 18/195,331, mailed on Nov. 29, 2021, 5 pages.
Notice of Allowance received for U.S. Appl. No. 18/195,331, mailed on Sep. 14, 2021, 9 pages.
Notice of Allowance received for U.S. Appl. No. 18/195,331, mailed on Apr. 2, 2024, 8 pages.
Office Action received for Australian Patent Application No. 2022202459, mailed on Jan. 6, 2023, 3 pages.
Office Action received for Australian Patent Application No. 2022202459, mailed on Mar. 27, 2023, 5 pages.
Office Action received for Australian Patent Application No. 2023212604, mailed on Sep. 4, 2023, 3 pages.
Office Action received for Chinese Patent Application No. 202210004176.9, mailed on Apr. 28, 2023, 12 pages.
Office Action received for Chinese Patent Application No. 202210004176.9, mailed on Feb. 19, 2023, 23 pages.
Office Action received for Chinese Patent Application No. 202210004176.9, mailed on Sep. 28, 2022, 12 pages.
Office Action received for Danish Patent Application No. PA201970534, mailed on Feb. 16, 2021, 2 pages.
Office Action received for Danish Patent Application No. PA201970534, mailed on Jun. 29, 2020, 2 pages.
Office Action received for Danish Pante Application No. PA202070335, mailed Jun. 11, 2021, 4 pages.
Office Action received for Danish Patent Application No. PA202070335, mailed on Nov. 17, 2021, 6 pages.
Office Action received for European Patent Application No. 20746438.9, mailed on Feb. 1, 2023, 9 pages.
Office Action received for European Patent Application No. 20746438.9, mailed on Jul. 4, 2023, 7 pages.
Office Action received for European Patent Application No. 20746438.9, mailed on Oct. 31, 2022, 7 pages.
Office Action received for European Patent Application No. 20746438.9, mailed on Oct. 31, 2023, 9 pages.
Office Action received for Japanese Patent Application No. 2022-078277, mailed on Jun. 9, 2023, 11 pages.
Office Action received for Korean Patent Application No. 10-2022-7012608, mailed on Dec. 5, 2023, 12 pages.
Search Report and Opinion received for Danish Patent Application No. PA201970534, mailed on Sep. 23, 2019, 6 pages.
Search Report and Opinion received for Danish Patent Application No. PA202070335, mailed on Nov. 27, 2020, 10 pages.
Select (SQL)—Wikipedia, Online available at: https://en.wikipedia.org/w/index.php?title=Select_(SQL)&direction=prev&oldid=489205430, Mar. 9, 2012, 5 pages.
STUDIOSIXDIGITAL," Dosimeter", Retrieved from URL: <https://studiosixdigital.com/audiotools-modules-2/spl-modules/dosimeter.html>, Mar. 3, 2017, 6 pages.
Extended European Search Report received for European Patent Application No. 24183014.0, mailed on Oct. 8, 2024, 9 pages.
Office Action received for Japanese Patent Application No. 2023-193034, mailed on Sep. 27, 2024, 8 pages (4 pages of English Translation and 4 pages of Official Copy).
Samsung Galaxy S5—User Manual, Available online at: https://www.att.com/support_static_files/manuals/Samsung_Galaxy_S5.pdf, Mar. 31, 2015, 214 pages.

\* cited by examiner

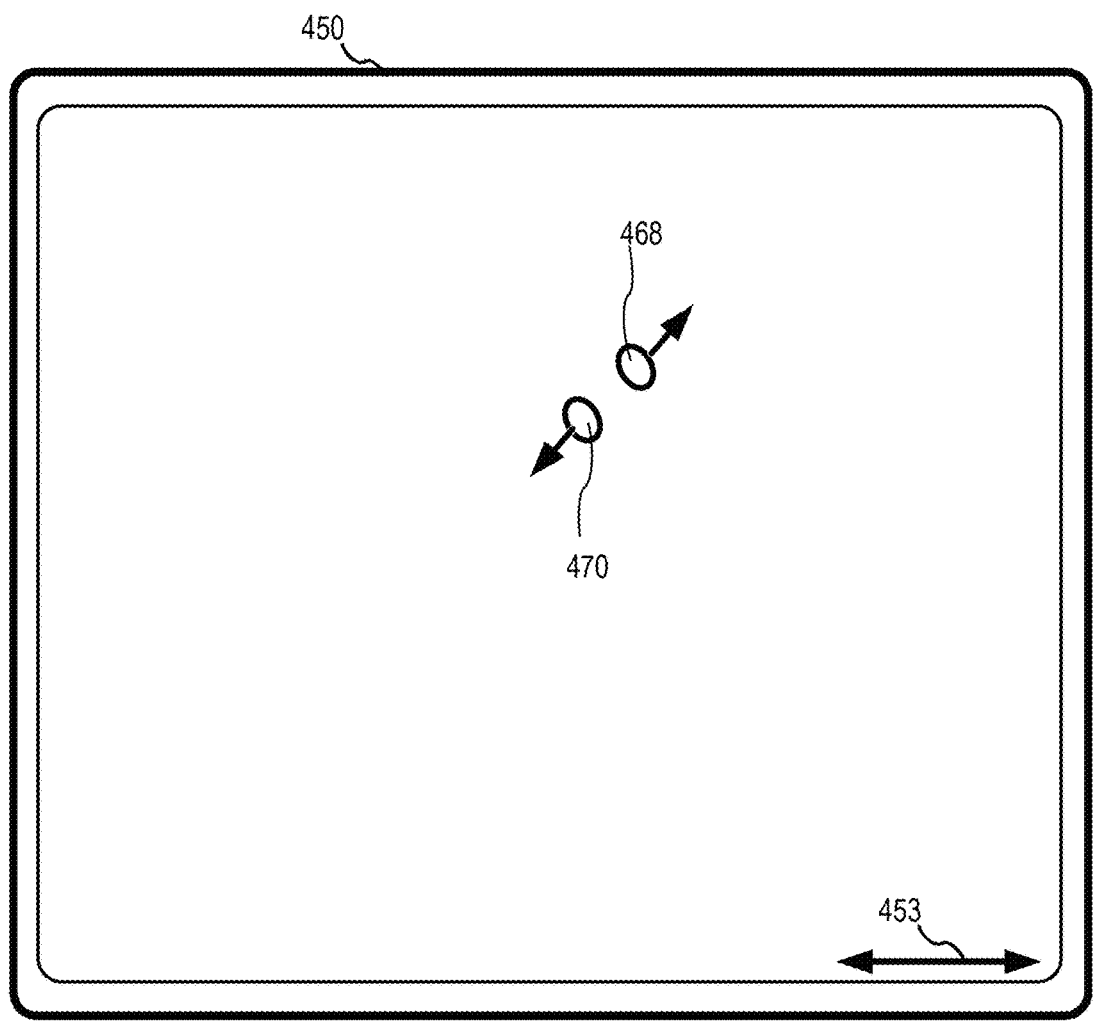
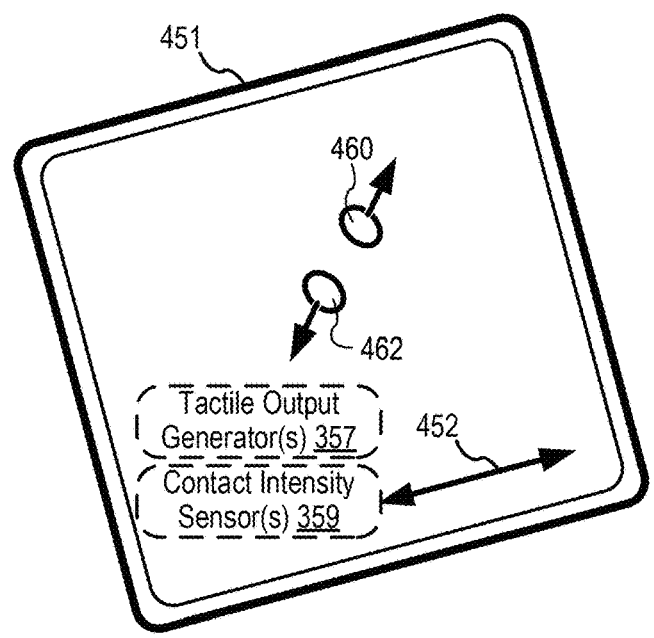
*FIG. 4B*

700 while a detected environmental noise level is at a first noise level:

702
in accordance with a determination that a set of one or more sound reduction criteria are met, display, via the display generation component, a first user interface that includes an indication that indicates a second noise level that is lower than the first noise level when a first user of the computer system is using a sound reduction device 704
in accordance with a determination that the set of one or more sound reduction criteria are not met, display, via the display generation component, a second user interface that indicates the first noise level

*FIG. 7*

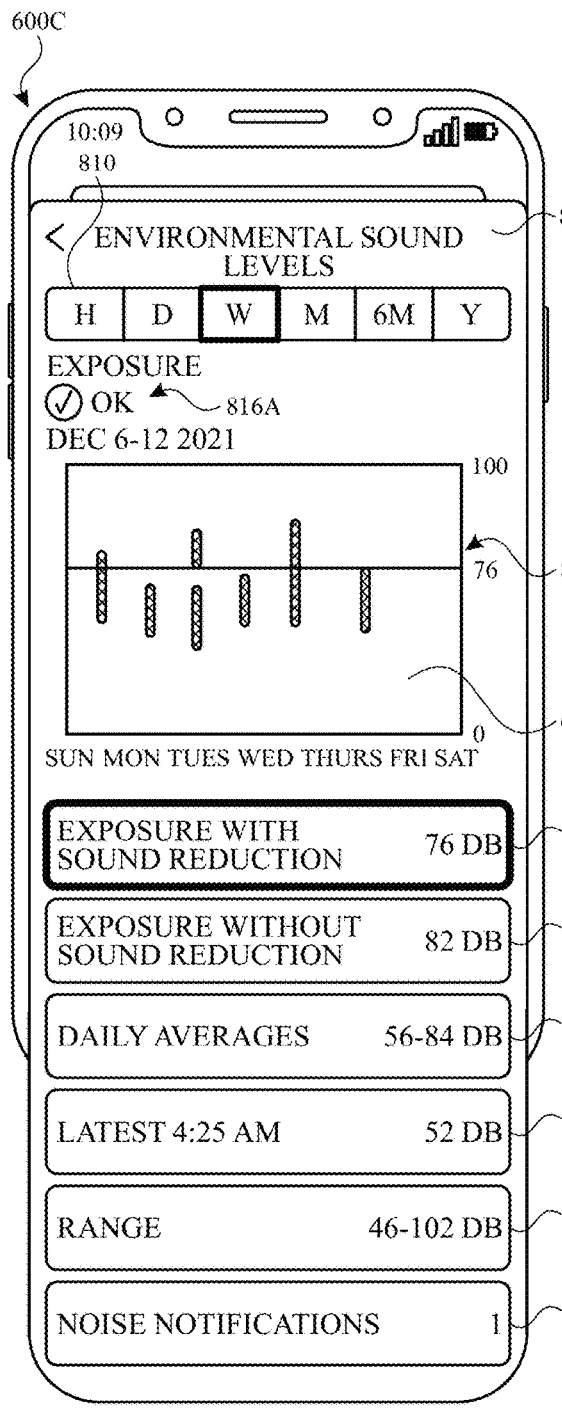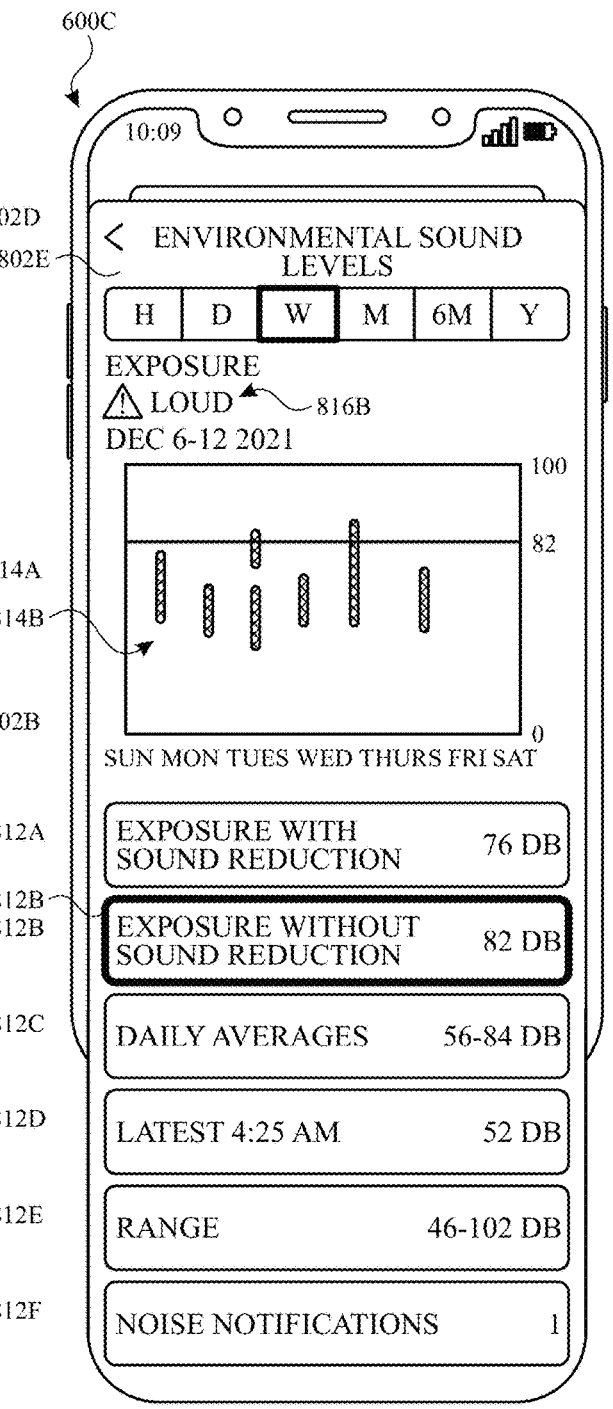
*FIG. 8D*  *FIG. 8E*

900

902
Display, via the display generation component, a representation of a noise level at a plurality of different times, wherein the representation includes:

In accordance with a determination that a sound reduction display option is enabled:

904
A first indication of a noise level at a first time of the plurality of different times that indicates:

In accordance with a determination that sound reduction was in effect at the first time, a first noise level, wherein the first noise level is based on an environmental noise level at the first time and a first sound reduction effect that was in effect at the first time In accordance with a determination that sound reduction was not in effect at the first time, a second noise level that is greater than the first noise level, wherein the second noise level is based on the environmental noise level at the first time

906
A second indication of a noise level at a second time of the plurality of different times that is different from the first time and that indicates:

In accordance with a determination that sound reduction was in effect at the second time, a third noise level, wherein the third noise level is based on an environmental noise level at the second time and a second sound reduction effect that was in effect at the second time In accordance with a determination that sound reduction was not in effect at the second time, a fourth noise level that is greater than the third noise level, wherein the fourth noise level is based on the environmental noise level at the second time

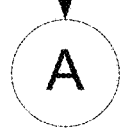

1002
Display via the display generation component, a representation of a noise level at a plurality of different times, wherein the representation includes: a first indication of a sound reduction level at a first time of the first plurality of times; and a second indication of a sound reduction level at a second time of the first plurality of times that is different from the first time

1004
While displaying the first representation, receiving, via the one or more input devices, a set of one or more inputs corresponding to selection of a display option for a second time period corresponding to a second plurality of times that is different from the first plurality of times;

1006
In response to receiving the set of one or more inputs, displaying, via the display generation component, a second representation of a sound reduction level at the second plurality of times, wherein the second representation includes: a third indication of a sound reduction level at a third time of the second plurality of times; and a fourth indication of a sound reduction level at a fourth time of the second plurality of times that is different from the third time; wherein: in accordance with a determination that the display option for the second time period corresponds to a first display option, the second time period is a subset of the first time period; and in accordance with a determination that the display option for the second time period corresponds to a second display option, the first time period is a subset of the second time period.

*FIG. 10*

METHODS AND USER INTERFACES FOR MONITORING SOUND REDUCTION

CROSS-REFERENCE TO RELATED APPLICATIONS

This application is a continuation of U.S. patent application Ser. No. 18/195,331, entitled "METHODS AND USER INTERFACES FOR MONITORING SOUND REDUCTION," filed May 9, 2023, which claims priority to U.S. Provisional Patent Application No. 63/342,623, entitled "METHODS AND USER INTERFACES FOR MONITORING SOUND REDUCTION," filed on May 16, 2022. The contents of each of these applications are incorporated herein by reference in their entirety.

FIELD

The present disclosure relates generally to computer user interfaces, and more specifically to techniques for managing and visualizing sound reduction.

BACKGROUND

An electronic device can be used to monitor a level of noise to which a user of the electronic device is exposed. The electronic device can also be used to monitor a sound reduction effect by another electronic device and a resulting sound reduction level. Information concerning the monitored noise exposure levels and the sound reduction effects can be presented to the user on the electronic device.

BRIEF SUMMARY

Some techniques for managing and visualizing sound reduction using electronic devices, however, are generally cumbersome and inefficient. For example, some existing techniques use a complex and time-consuming user interface, which may include multiple key presses or keystrokes and/or require viewing multiple separate interfaces to identify relevant information. Existing techniques require more time than necessary, wasting user time and device energy. This latter consideration is particularly important in battery-operated devices.

Accordingly, the present technique provides electronic devices with faster, more efficient methods and interfaces for managing and visualizing sound reduction. Such methods and interfaces optionally complement or replace other methods for managing and visualizing sound reduction. Such methods and interfaces reduce the cognitive burden on a user and produce a more efficient human-machine interface. For battery-operated computing devices, such methods and interfaces conserve power and increase the time between battery charges.

In accordance with some embodiments, a method performed at a computer system that is in communication with a display generation component is described. The method comprises: while a detected environmental noise level is at a first noise level: in accordance with a determination that a set of one or more sound reduction criteria are met, displaying, via the display generation component, a first user interface that includes an indication that indicates a second noise level that is lower than the first noise level when a first user of the computer system is using a sound reduction device; and in accordance with a determination that the set of one or more sound reduction criteria are not met, displaying, via the display generation component, a second user interface that indicates the first noise level.

In accordance with some embodiments, a non-transitory computer-readable storage medium is described. The non-transitory computer-readable storage medium stores one or more programs configured to be executed by one or more processors of a computer system that is in communication with a display generation component, the one or more programs including instructions for: while a detected environmental noise level is at a first noise level: in accordance with a determination that a set of one or more sound reduction criteria are met, displaying, via the display generation component, a user interface that includes an indication that indicates a second noise level that is lower than the first noise level when a first user of the computer system is using a sound reduction device; and in accordance with a determination that the set of one or more sound reduction criteria are not met, displaying, via the display generation component, a second user interface that indicates the first noise level.

In accordance with some embodiments, a transitory computer-readable storage medium is described. The transitory computer-readable storage medium stores one or more programs configured to be executed by one or more processors of a computer system that is in communication with a display generation component, the one or more programs including instructions for: while a detected environmental noise level is at a first noise level: in accordance with a determination that a set of one or more sound reduction criteria are met, displaying, via the display generation component, a user interface that includes an indication that indicates a second noise level that is lower than the first noise level when a first user of the computer system is using a sound reduction device; and in accordance with a determination that the set of one or more sound reduction criteria are not met, displaying, via the display generation component, a second user interface that indicates the first noise level.

In accordance with some embodiments, a computer system that is in communication with a display generation component is described. The computer system comprises: one or more processors; and memory storing one or more programs configured to be executed by the one or more processors, the one or more programs including instructions for: while a detected environmental noise level is at a first noise level: in accordance with a determination that a set of one or more sound reduction criteria are met, displaying, via the display generation component, a user interface that includes an indication that indicates a second noise level that is lower than the first noise level when a first user of the computer system is using a sound reduction device; and in accordance with a determination that the set of one or more sound reduction criteria are not met, displaying, via the display generation component, a second user interface that indicates the first noise level.

In accordance with some embodiments, a computer system that is in communication with a display generation component is described. The computer system comprises: means for, while a detected environmental noise level is at a first noise level: in accordance with a determination that a set of one or more sound reduction criteria are met, displaying, via the display generation component, a user interface that includes an indication that indicates a second noise level that is lower than the first noise level when a first user of the computer system is using a sound reduction device; and in accordance with a determination that the set of one or more sound reduction criteria are not met, displaying, via the display generation component, a second user interface that indicates the first noise level.

In accordance with some embodiments, a computer program product is described. The computer program product comprises one or more programs configured to be executed by one or more processors of a computer system that is in communication with a display generation component, the one or more programs including instructions for: while a detected environmental noise level is at a first noise level: in accordance with a determination that a set of one or more sound reduction criteria are met, displaying, via the display generation component, a use interface that includes an indication that indicates a second noise level that is lower than the first noise level when a first user of the computer system is using a sound reduction device; and in accordance with a determination that the set of one or more sound reduction criteria are not met, displaying, via the display generation component, a second user interface that indicates the first noise level.

In accordance with some embodiments, a method performed at a computer system that is in communication with a display generation component is described. The method comprises: displaying, via the display generation component, a representation of a noise level at a plurality of different times, wherein the representation includes: in accordance with a determination that a sound reduction display option is enabled: a first indication of a noise level at a first time of the plurality of different times that indicates: in accordance with a determination that sound reduction was in effect at the first time, a first noise level, wherein the first noise level is based on an environmental noise level at the first time and a first sound reduction effect that was in effect at the first time; and in accordance with a determination that sound reduction was not in effect at the first time, a second noise level that is greater than the first noise level, wherein the second noise level is based on the environmental noise level at the first time; a second indication of a noise level at a second time of the plurality of different times that is different from the first time and that indicates: in accordance with a determination that sound reduction was in effect at the second time, a third noise level, wherein the third noise level is based on an environmental noise level at the second time and a second sound reduction effect that was in effect at the second time; and in accordance with a determination that sound reduction was not in effect at the second time, a fourth noise level that is greater than the third noise level, wherein the fourth noise level is based on the environmental noise level at the second time; in accordance with a determination that the sound reduction display option is not enabled: a third indication of a noise level at the first time that indicates the second noise level; and a fourth indication of a noise level at the second time that indicates the fourth noise level.

In accordance with some embodiments, a non-transitory computer-readable storage medium is described. The non-transitory computer-readable storage medium stores one or more programs configured to be executed by one or more processors of a computer system that is in communication with a display generation component, the one or more programs including instructions for: displaying, via the display generation component, a representation of a noise level at a plurality of different times, wherein the representation includes: in accordance with a determination that a sound reduction display option is enabled: a first indication of a noise level at a first time of the plurality of different times that indicates: in accordance with a determination that sound reduction was in effect at the first time, a first noise level, wherein the first noise level is based on an environmental noise level at the first time and a first sound reduction effect that was in effect at the first time; and in accordance with a determination that sound reduction was not in effect at the first time, a second noise level that is greater than the first noise level, wherein the second noise level is based on the environmental noise level at the first time; a second indication of a noise level at a second time of the plurality of different times that is different from the first time and that indicates: in accordance with a determination that sound reduction was in effect at the second time, a third noise level, wherein the third noise level is based on an environmental noise level at the second time and a second sound reduction effect that was in effect at the second time; and in accordance with a determination that sound reduction was not in effect at the second time, a fourth noise level that is greater than the third noise level, wherein the fourth noise level is based on the environmental noise level at the second time; in accordance with a determination that the sound reduction display option is not enabled: a third indication of a noise level at the first time that indicates the second noise level; and a fourth indication of a noise level at the second time that indicates the fourth noise level.

In accordance with some embodiments, a transitory computer-readable storage medium is described. The transitory computer-readable storage medium stores one or more programs configured to be executed by one or more processors of a computer system that is in communication with a display generation component, the one or more programs including instructions for: displaying, via the display generation component, a representation of a noise level at a plurality of different times, wherein the representation includes: in accordance with a determination that a sound reduction display option is enabled: a first indication of a noise level at a first time of the plurality of different times that indicates: in accordance with a determination that sound reduction was in effect at the first time, a first noise level, wherein the first noise level is based on an environmental noise level at the first time and a first sound reduction effect that was in effect at the first time; and in accordance with a determination that sound reduction was not in effect at the first time, a second noise level that is greater than the first noise level, wherein the second noise level is based on the environmental noise level at the first time; a second indication of a noise level at a second time of the plurality of different times that is different from the first time and that indicates: in accordance with a determination that sound reduction was in effect at the second time, a third noise level, wherein the third noise level is based on an environmental noise level at the second time and a second sound reduction effect that was in effect at the second time; and in accordance with a determination that sound reduction was not in effect at the second time, a fourth noise level that is greater than the third noise level, wherein the fourth noise level is based on the environmental noise level at the second time; in accordance with a determination that the sound reduction display option is not enabled: a third indication of a noise level at the first time that indicates the second noise level; and a fourth indication of a noise level at the second time that indicates the fourth noise level.

In accordance with some embodiments, a computer system that is in communication with a display generation component is described. The computer system comprises: one or more processors; and memory storing one or more programs configured to be executed by the one or more processors, the one or more programs including instructions for: displaying, via the display generation component, a representation of a noise level at a plurality of different times, wherein the representation includes: in accordance with a determination that a sound reduction display option is enabled: a first indication of a noise level at a first time of the plurality of different times that indicates: in accordance with a determination that sound reduction was in effect at the first time, a first noise level, wherein the first noise level is based on an environmental noise level at the first time and a first sound reduction effect that was in effect at the first time; and in accordance with a determination that sound reduction was not in effect at the first time, a second noise level that is greater than the first noise level, wherein the second noise level is based on the environmental noise level at the first time; a second indication of a noise level at a second time of the plurality of different times that is different from the first time and that indicates: in accordance with a determination that sound reduction was in effect at the second time, a third noise level, wherein the third noise level is based on an environmental noise level at the second time and a second sound reduction effect that was in effect at the second time; and in accordance with a determination that sound reduction was not in effect at the second time, a fourth noise level that is greater than the third noise level, wherein the fourth noise level is based on the environmental noise level at the second time; in accordance with a determination that the sound reduction display option is not enabled: a third indication of a noise level at the first time that indicates the second noise level; and a fourth indication of a noise level at the second time that indicates the fourth noise level.

In accordance with some embodiments, a computer system that is in communication with a display generation component is described. The computer system comprises: means for displaying, via the display generation component, a representation of a noise level at a plurality of different times, wherein the representation includes: in accordance with a determination that a sound reduction display option is enabled: a first indication of a noise level at a first time of the plurality of different times that indicates: in accordance with a determination that sound reduction was in effect at the first time, a first noise level, wherein the first noise level is based on an environmental noise level at the first time and a first sound reduction effect that was in effect at the first time; and in accordance with a determination that sound reduction was not in effect at the first time, a second noise level that is greater than the first noise level, wherein the second noise level is based on the environmental noise level at the first time; a second indication of a noise level at a second time of the plurality of different times that is different from the first time and that indicates: in accordance with a determination that sound reduction was in effect at the second time, a third noise level, wherein the third noise level is based on an environmental noise level at the second time and a second sound reduction effect that was in effect at the second time; and in accordance with a determination that sound reduction was not in effect at the second time, a fourth noise level that is greater than the third noise level, wherein the fourth noise level is based on the environmental noise level at the second time; in accordance with a determination that the sound reduction display option is not enabled: a third indication of a noise level at the first time that indicates the second noise level; and a fourth indication of a noise level at the second time that indicates the fourth noise level.

In accordance with some embodiments, a computer program product is described. The computer program product comprises one or more programs configured to be executed by one or more processors of a computer system that is in communication with a display generation component, the one or more programs including instructions for: displaying, via the display generation component, a representation of a noise level at a plurality of different times, wherein the representation includes: in accordance with a determination that a sound reduction display option is enabled: a first indication of a noise level at a first time of the plurality of different times that indicates: in accordance with a determination that sound reduction was in effect at the first time, a first noise level, wherein the first noise level is based on an environmental noise level at the first time and a first sound reduction effect that was in effect at the first time; and in accordance with a determination that sound reduction was not in effect at the first time, a second noise level that is greater than the first noise level, wherein the second noise level is based on the environmental noise level at the first time; a second indication of a noise level at a second time of the plurality of different times that is different from the first time and that indicates: in accordance with a determination that sound reduction was in effect at the second time, a third noise level, wherein the third noise level is based on an environmental noise level at the second time and a second sound reduction effect that was in effect at the second time; and in accordance with a determination that sound reduction was not in effect at the second time, a fourth noise level that is greater than the third noise level, wherein the fourth noise level is based on the environmental noise level at the second time; in accordance with a determination that the sound reduction display option is not enabled: a third indication of a noise level at the first time that indicates the second noise level; and a fourth indication of a noise level at the second time that indicates the fourth noise level.

In accordance with some embodiments, a method performed at a computer system that is in communication with a display generation component and one or more input devices is described. The method comprises: displaying, via the display generation component, a first representation of a sound reduction level for a first time period corresponding to a first plurality of times, wherein the first representation includes: a first indication of a sound reduction level at a first time of the first plurality of times; and a second indication of a sound reduction level at a second time of the first plurality of times that is different from the first time; while displaying the first representation, receiving, via the one or more input devices, a set of one or more inputs corresponding to selection of a display option for a second time period corresponding to a second plurality of times that is different from the first plurality of times; in response to receiving the set of one or more inputs, displaying, via the display generation component, a second representation of a sound reduction level at the second plurality of times, wherein the second representation includes: a third indication of a sound reduction level at a third time of the second plurality of times; and a fourth indication of a sound reduction level at a fourth time of the second plurality of times that is different from the third time; wherein: in accordance with a determination that the display option for the second time period corresponds to a first display option, the second time period is a subset of the first time period; and in accordance with a determination that the display option for the second time period corresponds to a second display option, the first time period is a subset of the second time period.

In accordance with some embodiments, a non-transitory computer-readable storage medium is described. The non-transitory computer readable storage medium stores one or more programs configured to be executed by one or more processors of a computer system that is in communication with a display generation component and one or more input devices, the one or more programs including instructions for: displaying, via the display generation component, a first representation of a sound reduction level for a first time period corresponding to a first plurality of times, wherein the first representation includes: a first indication of a sound reduction level at a first time of the first plurality of times; and a second indication of a sound reduction level at a second time of the first plurality of times that is different from the first time; while displaying the first representation, receiving, via the one or more input devices, a set of one or more inputs corresponding to selection of a display option for a second time period corresponding to a second plurality of times that is different from the first plurality of times; in response to receiving the set of one or more inputs, displaying, via the display generation component, a second representation of a sound reduction level at the second plurality of times, wherein the second representation includes: a third indication of a sound reduction level at a third time of the second plurality of times; and a fourth indication of a sound reduction level at a fourth time of the second plurality of times that is different from the third time; wherein: in accordance with a determination that the display option for the second time period corresponds to a first display option, the second time period is a subset of the first time period; and in accordance with a determination that the display option for the second time period corresponds to a second display option, the first time period is a subset of the second time period.

In accordance with some embodiments, a transitory computer-readable storage medium is described. The transitory computer readable storage medium stores one or more programs configured to be executed by one or more processors of a computer system that is in communication with a display generation component and one or more input devices, the one or more programs including instructions for: displaying, via the display generation component, a first representation of a sound reduction level for a first time period corresponding to a first plurality of times, wherein the first representation includes: a first indication of a sound reduction level at a first time of the first plurality of times; and a second indication of a sound reduction level at a second time of the first plurality of times that is different from the first time; while displaying the first representation, receiving, via the one or more input devices, a set of one or more inputs corresponding to selection of a display option for a second time period corresponding to a second plurality of times that is different from the first plurality of times; in response to receiving the set of one or more inputs, displaying, via the display generation component, a second representation of a sound reduction level at the second plurality of times, wherein the second representation includes: a third indication of a sound reduction level at a third time of the second plurality of times; and a fourth indication of a sound reduction level at a fourth time of the second plurality of times that is different from the third time; wherein: in accordance with a determination that the display option for the second time period corresponds to a first display option, the second time period is a subset of the first time period; and in accordance with a determination that the display option for the second time period corresponds to a second display option, the first time period is a subset of the second time period.

In accordance with some embodiments, a computer system that is in communication with a display generation component and one or more input devices is described. The computer system comprises: one or more processors; and memory storing one or more programs configured to be executed by the one or more processors, the one or more programs including instructions for: displaying, via the display generation component, a first representation of a sound reduction level for a first time period corresponding to a first plurality of times, wherein the first representation includes: a first indication of a sound reduction level at a first time of the first plurality of times; and a second indication of a sound reduction level at a second time of the first plurality of times that is different from the first time; while displaying the first representation, receiving, via the one or more input devices, a set of one or more inputs corresponding to selection of a display option for a second time period corresponding to a second plurality of times that is different from the first plurality of times; in response to receiving the set of one or more inputs, displaying, via the display generation component, a second representation of a sound reduction level at the second plurality of times, wherein the second representation includes: a third indication of a sound reduction level at a third time of the second plurality of times; and a fourth indication of a sound reduction level at a fourth time of the second plurality of times that is different from the third time; wherein: in accordance with a determination that the display option for the second time period corresponds to a first display option, the second time period is a subset of the first time period; and in accordance with a determination that the display option for the second time period corresponds to a second display option, the first time period is a subset of the second time period.

In accordance with some embodiments, a computer system that is in communication with a display generation component and one or more input devices is described. The computer system comprises: means for displaying, via the display generation component, a first representation of a sound reduction level for a first time period corresponding to a first plurality of times, wherein the first representation includes: a first indication of a sound reduction level at a first time of the first plurality of times; and a second indication of a sound reduction level at a second time of the first plurality of times that is different from the first time; means for, while displaying the first representation, receiving, via the one or more input devices, a set of one or more inputs corresponding to selection of a display option for a second time period corresponding to a second plurality of times that is different from the first plurality of times; means for, in response to receiving the set of one or more inputs, displaying, via the display generation component, a second representation of a sound reduction level at the second plurality of times, wherein the second representation includes: a third indication of a sound reduction level at a third time of the second plurality of times; and a fourth indication of a sound reduction level at a fourth time of the second plurality of times that is different from the third time; wherein: in accordance with a determination that the display option for the second time period corresponds to a first display option, the second time period is a subset of the first time period; and in accordance with a determination that the display option for the second time period corresponds to a second display option, the first time period is a subset of the second time period.

In accordance with some embodiments, a computer program product is described. The computer program product comprises one or more programs configured to be executed by one or more processors of a computer system that is in communication with a display generation component and one or more input devices, the one or more programs including instructions for: displaying, via the display generation component, a first representation of a sound reduction level for a first time period corresponding to a first plurality of times, wherein the first representation includes: a first indication of a sound reduction level at a first time of the first plurality of times; and a second indication of a sound reduction level at a second time of the first plurality of times that is different from the first time; while displaying the first representation, receiving, via the one or more input devices, a set of one or more inputs corresponding to selection of a display option for a second time period corresponding to a second plurality of times that is different from the first plurality of times; in response to receiving the set of one or more inputs, displaying, via the display generation component, a second representation of a sound reduction level at the second plurality of times, wherein the second representation includes: a third indication of a sound reduction level at a third time of the second plurality of times; and a fourth indication of a sound reduction level at a fourth time of the second plurality of times that is different from the third time; wherein: in accordance with a determination that the display option for the second time period corresponds to a first display option, the second time period is a subset of the first time period; and in accordance with a determination that the display option for the second time period corresponds to a second display option, the first time period is a subset of the second time period.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for managing and visualizing sound reduction, thereby increasing the effectiveness, efficiency, and user satisfaction with such devices. Such methods and interfaces may complement or replace other methods for managing and visualizing sound reduction.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

FIG. 7 is a flow diagram illustrating a method of monitoring noise exposure levels using a computer system, in accordance with some embodiments.

FIGS. 8C-8E illustrate exemplary user interfaces for monitoring noise exposure levels with and without a sound reduction effect.

FIGS. 9A-9B are a flow diagram illustrating a method of monitoring noise exposure levels with and without a sound reduction effect in accordance with some embodiments.

FIG. 10 is a flow diagram illustrating a method of monitoring sound reduction levels in accordance with some embodiments.

DESCRIPTION OF EMBODIMENTS

Figure 1A:
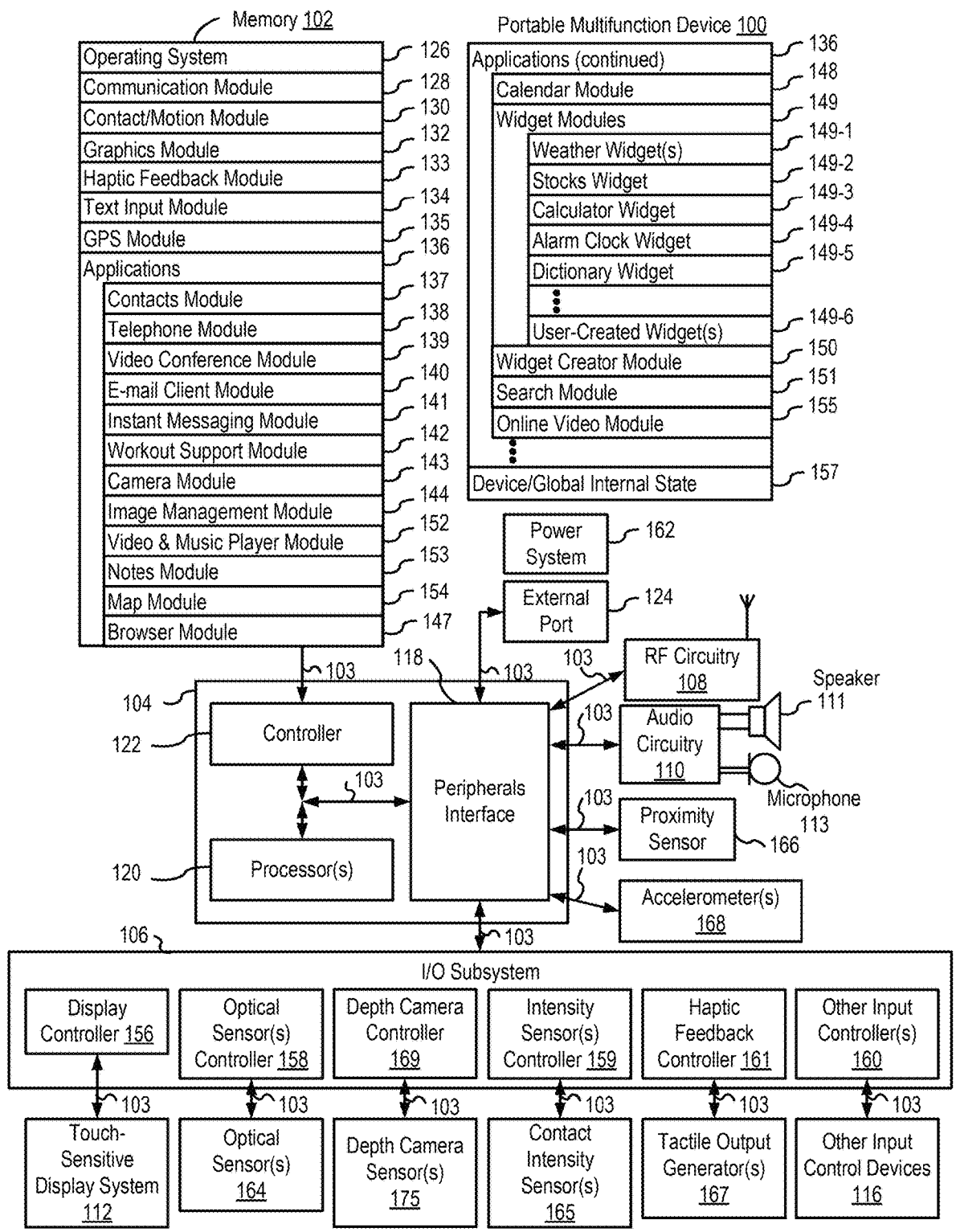
FIG. 1A is a block diagram illustrating a portable multifunction device with a touch-sensitive display in accordance with some embodiments.

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for managing and visualizing sound reduction. For example, there is a need for an electronic device that provides a user with information about the level of noise the user is exposed to in an easily understandable and convenient manner. In another example, there is a need for an electronic device that effectively alerts the user of the electronic device when the noise level that the user is exposed to exceeds a certain threshold level. In another example, there is a need for an electronic device that effectively alerts the user that the noise level the user is exposed to is being reduced by a sound reduction device and that without the sound reduction device the noise level would be unsafe. In another example, there is a need for an electronic device that provides a user with information about the level of noise reduction the user's sound reduction device is yielding. Such techniques can reduce the cognitive burden on a user who manages noise exposure levels, sound reduction levels, and sound reduction effects, thereby enhancing productivity. Further, such techniques can reduce processor and battery power otherwise wasted on redundant user inputs.

Below, FIGS. 1A-1B, 2, 3, 4A-4B, and 5A-5B, 6A-6I, 7, 8A-8H, 9A-9B, and 10 provide a description of exemplary devices for performing the techniques for monitoring noise exposure levels, sound reduction levels, and sound reduction effects. FIGS. 6A-6I illustrate exemplary user interfaces for monitoring noise exposure levels and noise-related notifications. FIG. 7 is a flow diagram illustrating a method of monitoring noise exposure levels using a computer system, in accordance with some embodiments. The user interfaces in FIGS. 6A-6I are used to illustrate the processes described below, including the processes in FIG. 7. FIGS. 8A-8H illustrate exemplary user interfaces for monitoring noise exposure levels with and without a sound reduction effect. FIGS. 9A-9B are a flow diagram illustrating a method of monitoring noise exposure levels with and without a sound reduction effect in accordance with some embodiments. FIG. 10 is a flow diagram illustrating a method of monitoring sound reduction levels in accordance with some embodiments. The user interfaces in FIGS. 8A-8H are used to illustrate the processes described below, including the processes in FIGS. 9A-9B.

The processes described below enhance the operability of the devices and make the user-device interfaces more efficient (e.g., by helping the user to provide proper inputs and reducing user mistakes when operating/interacting with the device) through various techniques, including by providing improved visual feedback to the user, reducing the number of inputs needed to perform an operation, providing additional control options without cluttering the user interface with additional displayed controls, performing an operation when a set of conditions has been met without requiring further user input, and/or additional techniques. These techniques also reduce power usage and improve battery life of the device by enabling the user to use the device more quickly and efficiently.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

Although the following description uses terms "first," "second," etc. to describe various elements, these elements should not be limited by the terms. In some embodiments, these terms are used to distinguish one element from another. For example, a first touch could be termed a second touch, and, similarly, a second touch could be termed a first touch, without departing from the scope of the various described embodiments. In some embodiments, the first touch and the second touch are two separate references to the same touch. In some embodiments, the first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs (such as computer programs (e.g., including instructions)) and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VOIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2).

The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures and/or air gestures) as input. In some embodiments, the one or more input devices are integrated with the computer system. In some embodiments, the one or more input devices are separate from the computer system. In some embodiments, an air gesture is a gesture that is detected without the user touching an input element that is part of the device (or independently of an input element that is a part of the device) and is based on detected motion of a portion of the user's body through the air including motion of the user's body relative to an absolute reference (e.g., an angle of the user's arm relative to the ground or a distance of the user's hand relative to the ground), relative to another portion of the user's body (e.g., movement of a hand of the user relative to a shoulder of the user, movement of one hand of the user relative to another hand of the user, and/or movement of a finger of the user relative to another finger or portion of a hand of the user), and/or absolute motion of a portion of the user's body (e.g., a tap gesture that includes movement of a hand in a predetermined pose by a predetermined amount and/or speed, or a shake gesture that includes a predetermined speed or amount of rotation of a portion of the user's body).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
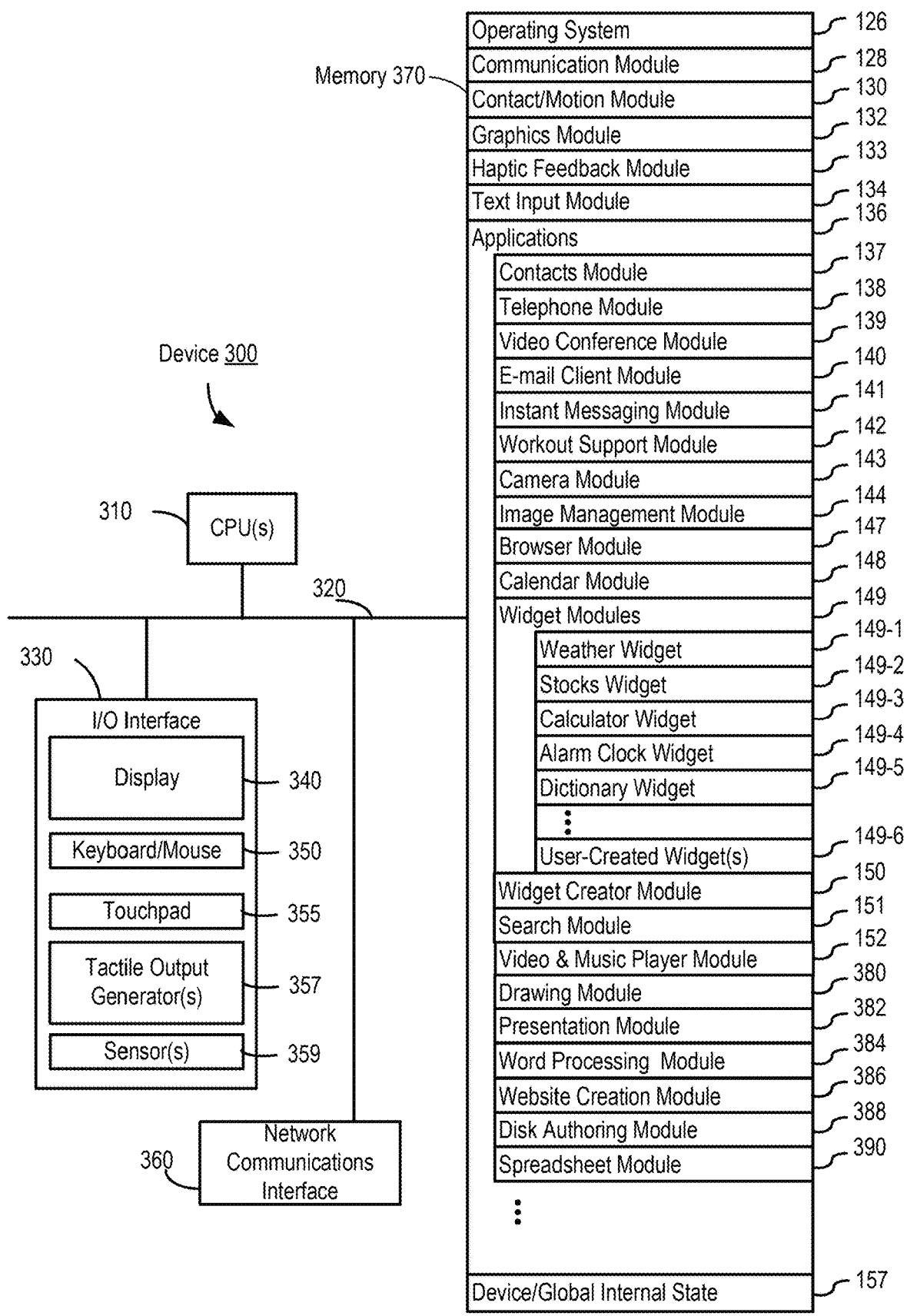
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, IOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail client module 140, Instant messaging (IM) module 141, browser module 147, and any other application that needs text input).

GPS module 135 determines the location of the device and provides this information for use in various applications (e.g., to telephone module 138 for use in location-based dialing; to imaging module 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  IM module 141;
  Workout support module 142;
  Imaging module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone module 138, video conference module 139, e-mail client module 140, or IM module 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with imaging module 143.

In conjunction with RF circuitry 108, touch screen 112, display controller 156, contact/motion module 130, graphics module 132, and text input module 134, the IM module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, imaging module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and imaging module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, IM module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs (such as computer programs (e.g., including instructions)), procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
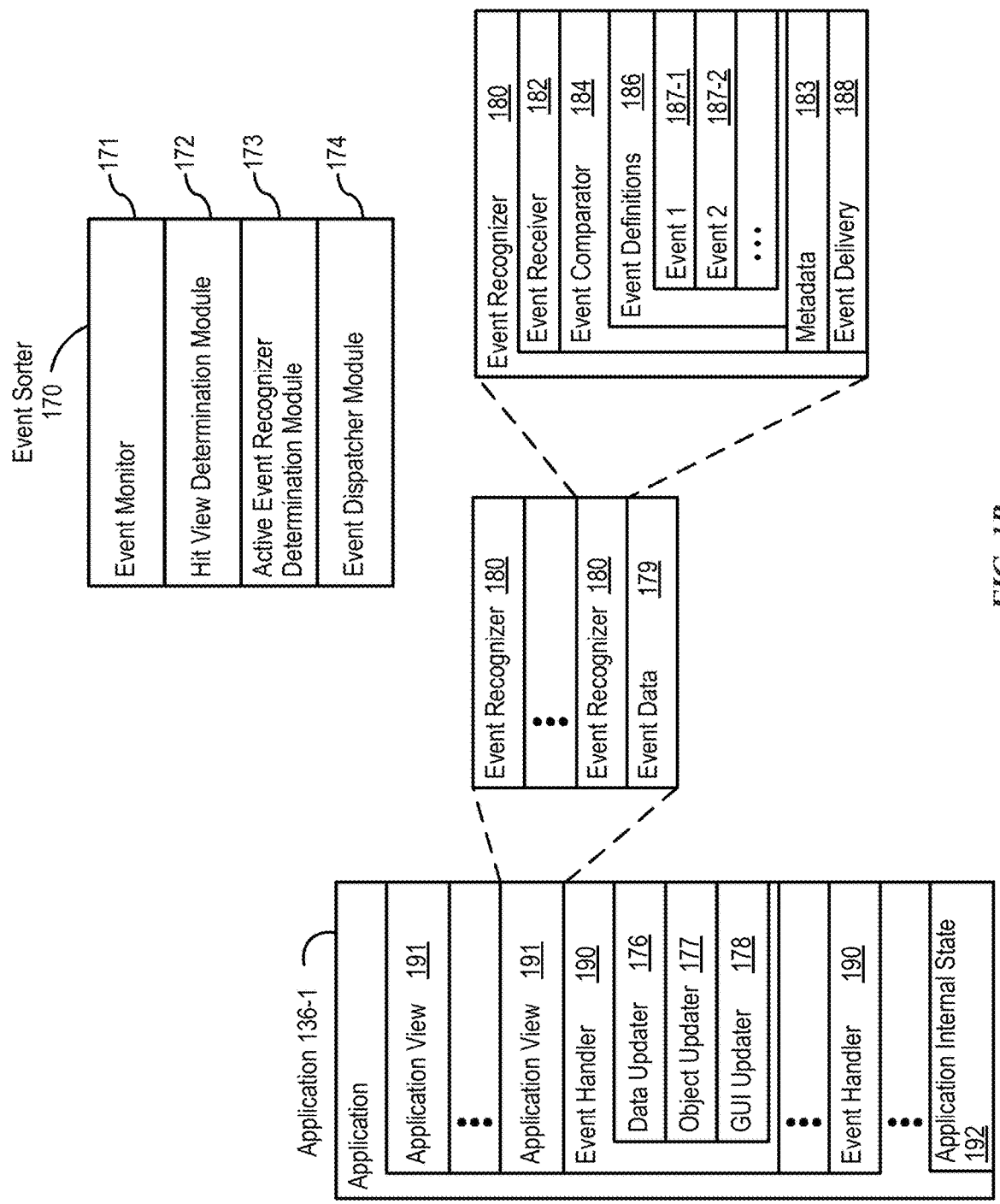
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (e.g., 187-1 and/or 187-2) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definitions 186 include a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
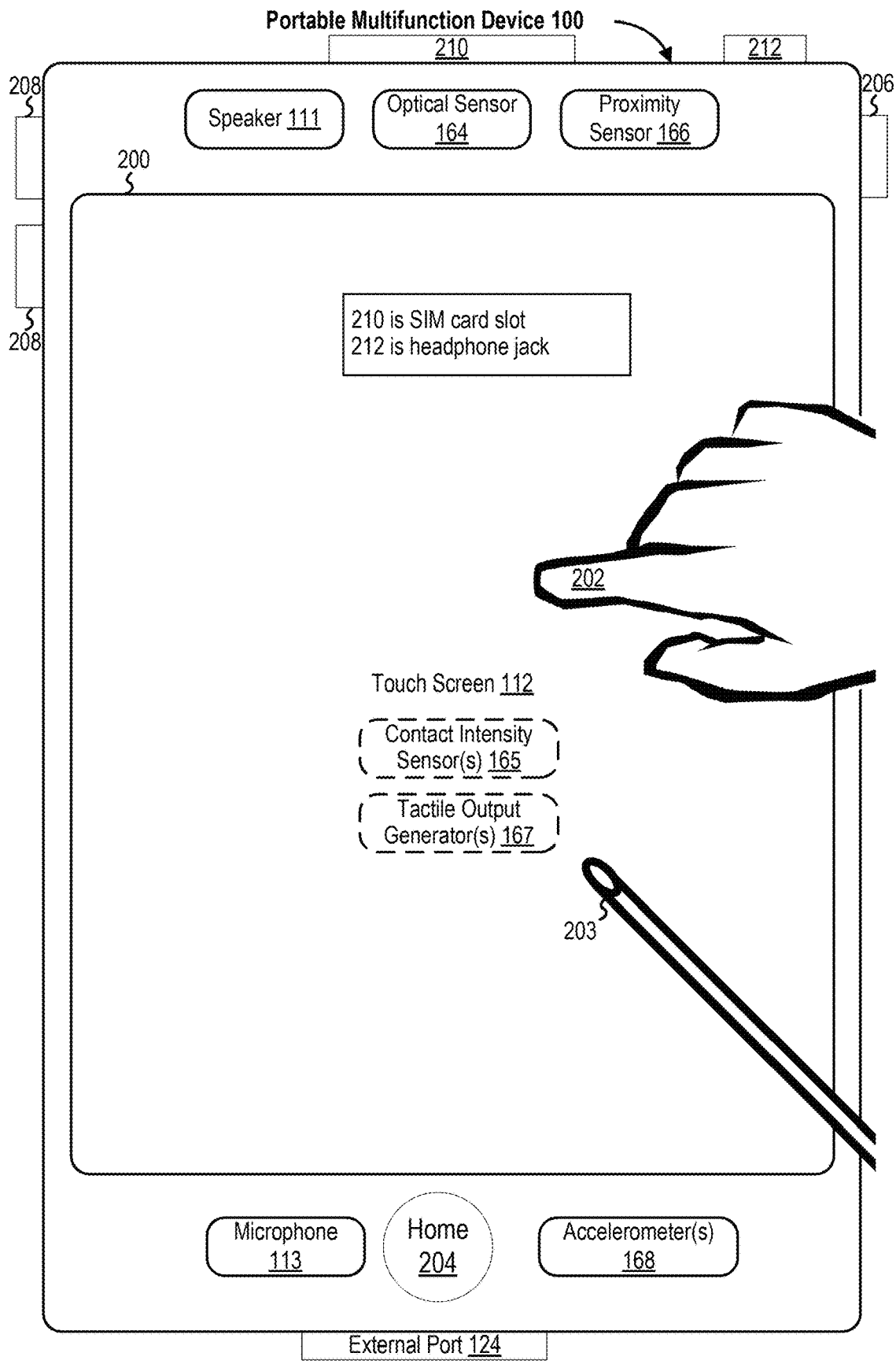
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or computer programs (e.g., sets of instructions or including instructions) need not be implemented as separate software programs (such as computer programs (e.g., including instructions)), procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
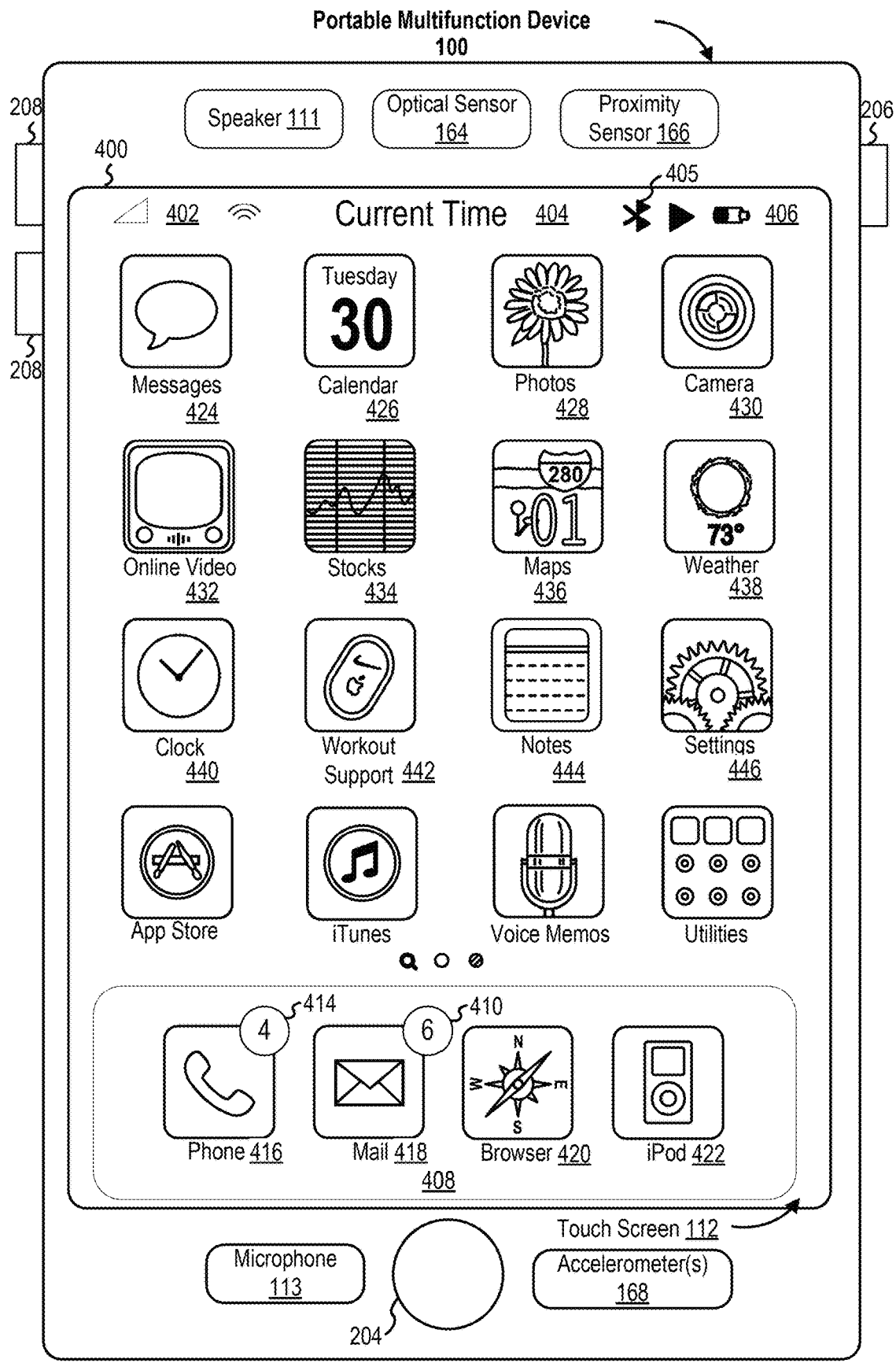
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
　Icon 416 for telephone module 138, labeled "Phone," which optionally includes an indicator 414 of the number of missed calls or voicemail messages;
　Icon 418 for e-mail client module 140, labeled "Mail," which optionally includes an indicator 410 of the number of unread e-mails;
　Icon 420 for browser module 147, labeled "Browser;" and
　Icon 422 for video and music player module 152, also referred to as iPod (trademark of Apple Inc.) module 152, labeled "iPod;" and
Icons for other applications, such as:
　Icon 424 for IM module 141, labeled "Messages;"
　Icon 426 for calendar module 148, labeled "Calendar;"
　Icon 428 for image management module 144, labeled "Photos;"
　Icon 430 for imaging module 143, labeled "Camera;"
　Icon 432 for online video module 155, labeled "Online Video;"
　Icon 434 for stocks widget 149-2, labeled "Stocks;"
　Icon 436 for map module 154, labeled "Maps;"
　Icon 438 for weather widget 149-1, labeled "Weather;"
　Icon 440 for alarm clock widget 149-4, labeled "Clock;"
　Icon 442 for workout support module 142, labeled "Workout Support;"
　Icon 444 for notes module 153, labeled "Notes;" and
　Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
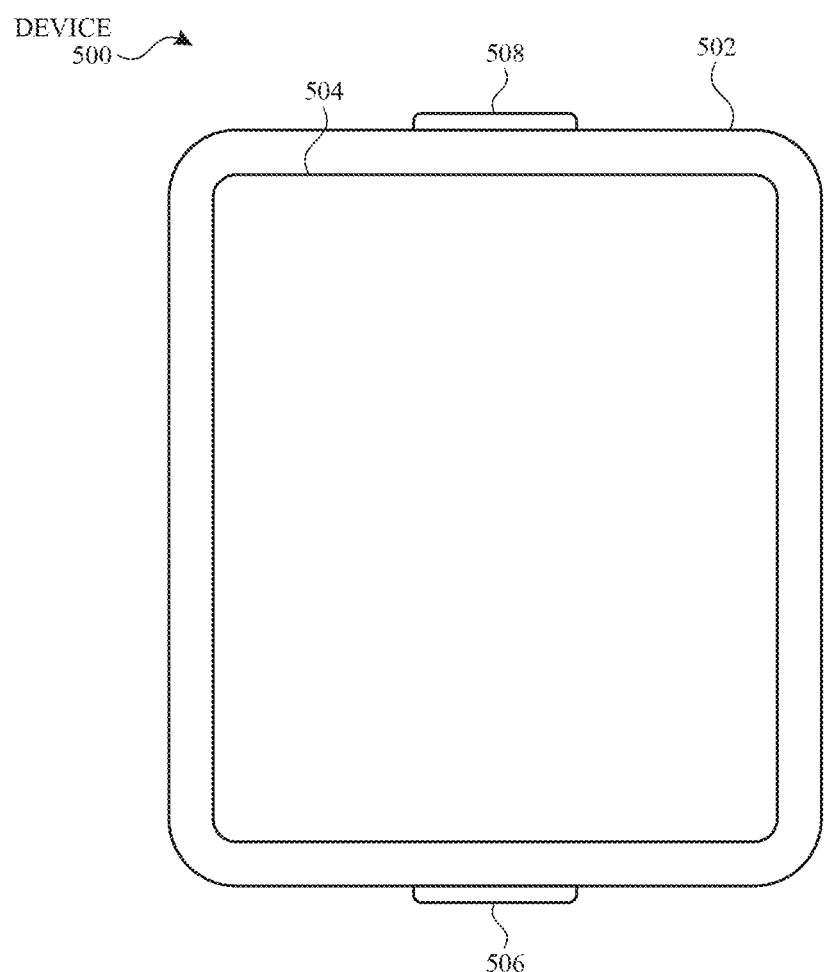
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
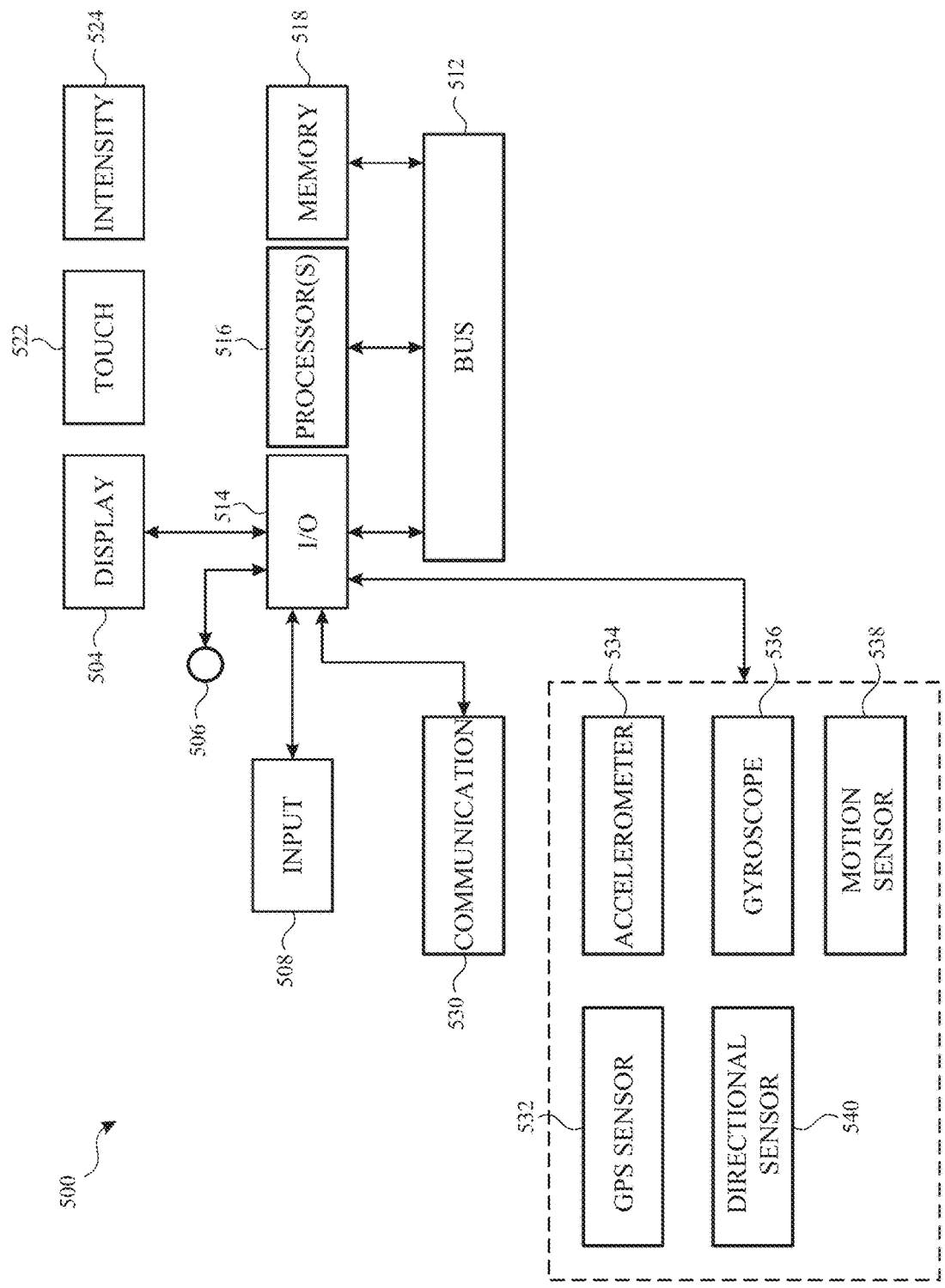
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700, 900, and 1000 (FIGS. 7, 9A-9B, and 10). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:

an active application, which is currently displayed on a display screen of the device that the application is being used on;

a background application (or background processes), which is not currently displayed, but one or more processes for the application are being processed by one or more processors; and a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on an electronic device, such as portable multifunction device 100, device 300, or device 500.

FIGS. 6A-6I illustrate exemplary user interfaces for monitoring sound exposure levels, in accordance with some embodiments. The user interfaces in these figures are used to illustrate the processes described below, including the processes in FIG. 7.

Figure 6A:
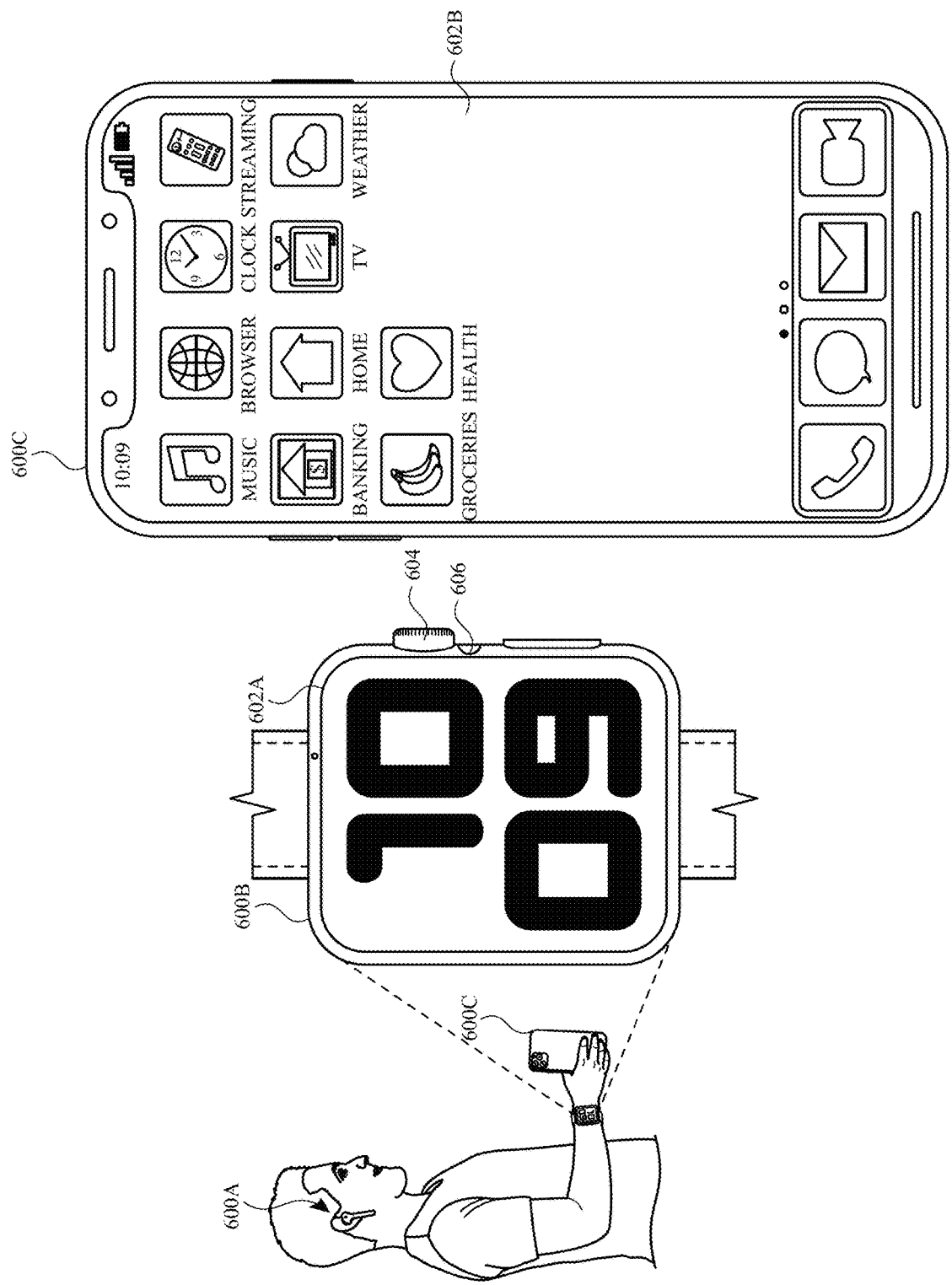
FIGS. 6A-6B illustrate exemplary components and user interfaces of personal electronic devices in accordance with some embodiments.

FIG. 6A illustrates a user who is wearing headphones 600A, watch 600B, and using phone 600C. Headphones 600A are equipped with a sound reduction feature that can be selectively and/or automatically enabled or disabled. When enabled, the sound reduction feature can reduce the level of noise experienced by the user. For example, while the environmental noise is at a first level, e.g., 80 decibels (due to loud traffic noise), the user experiences only 60 decibels of noise when the feature is enabled. If the user disables the feature in that same environment, he would experience the unmodified 80 decibels of noise. In some embodiments, headphones 600A also includes one or more microphones for detecting audio commands from the user and/or to measure environmental noise levels. Watch 600B includes a display 602A, which in FIG. 6A, displays the current time. Watch 600B also includes rotatable and depressible input mechanism 604 (e.g., rotatable and depressible in relation to a housing or frame of the device), and a microphone 606 for detecting audio commands from the user and/or to measure environmental noise levels. Phone 600C includes display 602B, which in FIG. 6A, is displaying a home screen.

In some embodiments, headphones 600A includes one or more features of devices 100, 300, and/or 500. In some embodiments, watch 600B includes one or more features of devices 100, 300, and/or 500. In some embodiments, phone 600C includes one or more features of devices 100, 300, and/or 500. In some embodiments, headphones 600A are a wearable electronic device (e.g., earbuds, in-car listening devices) that include sound generation and sound reduction functions. In some embodiments, headphones 600A generate an active and/or dynamic sound reduction effect (e.g., the headphones 600A generate varying levels of sound reduction in response to varying levels of environmental sound). In some embodiments, headphones 600A generate a constant sound reduction effect (e.g., via mechanical/physical structures of the headphones). In some embodiments, headphones 600A generate a sound reduction effect when a sound reduction function for headphones 600A is enabled, and do not generate a sound reduction effect when the sound reduction function is not enabled.

Figure 6B:
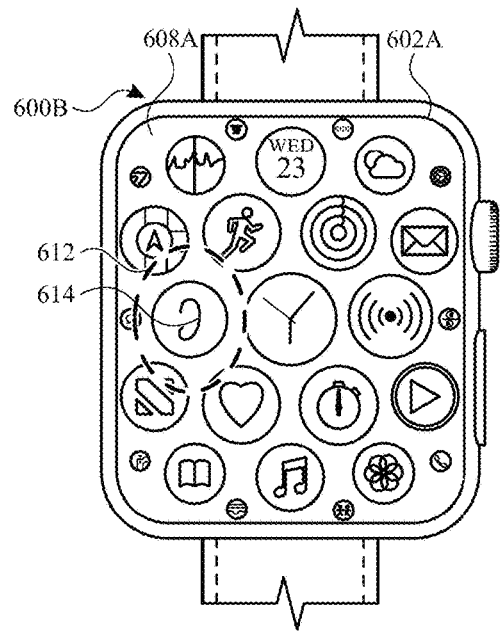

As depicted in FIG. 6B, home user interface 608A on watch 600B includes multiple affordances, each affordance associated with an application stored on watch 600B. For example, noise affordance 614 launches a noise monitoring application. FIG. 6B depicts watch 600B receiving user input 612 (e.g., a tap) on noise affordance 614. In response to receiving user input 612, device 600 displays user interface 610A (e.g., an interface associated with the noise application), as depicted in FIG. 6C.

Figure 6C:
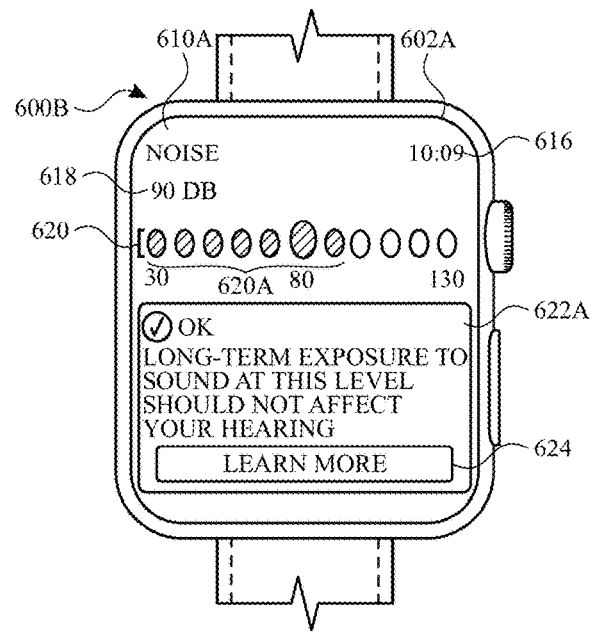
FIGS. 6C-6I illustrate exemplary user interfaces for monitoring noise exposure levels and noise-related notifications in accordance with some embodiments.

FIG. 6C depicts noise user interface 610A on watch 600B while the sound reduction function of headphones 600A is not enabled and the user is in an environment where the ambient noise level is 90 dB (e.g., without any sound reduction). In FIG. 6C, noise user interface 601A includes indication of time 616 (e.g., indicating a current time of 10:09), noise level indicator 618, noise meter indicator 620, and noise status indicator 622A. Noise level indicator 618 provides a numeric indication (e.g., indicating a current noise level of 90 dB) of a first noise level value (e.g., measured by or determined by watch 600B based on noise data identified by microphone 606) that is experienced by a user of watch 600B without a sound reduction effect (e.g., noise cancellation sound reduction via headphones 600A); this level can also be referred to as an environmental and/or unmodified noise level. Noise status indicator 622A provides a non-numeric indication (e.g., an indication including text and/or graphics) of the first noise level value (e.g., measured by or determined by watch 600B from noise data derived from microphone 606) relative to a first noise level threshold (e.g., a safe noise level threshold, a predetermined 90 dB threshold) and selectable option 624. Selectable option 624 can be selected by an input to present additional information related to hearing health (e.g., a description of the long term exposure effects of sound levels above a threshold value). In some embodiments, the first noise level threshold is user-configurable. In some embodiments, watch 600B identifies a noise level based on noise data detected by a sensor (e.g., microphone 606) of the watch 600B (e.g., the first noise level represents a noise level of the physical environment (e.g., environmental noise level) where watch 600B is located).

Noise meter indicator 620 provides a graphical indication of a second noise level (e.g., measured by watch 600B via microphone 606) that corresponds to the noise level indicated by noise level indicator 618. In some embodiments, the second noise level and the first noise level are the same noise level. In some embodiments, the first noise level and the second noise level are determined based on common noise data sampled at different time periods and/or rates (e.g., 1-second and 0.1-seconds, respectively). Noise meter indicator 620 includes active portion 620A (e.g., a visually emphasized portion) that varies in size and/or color according to the second noise level. As illustrated by the following figures, the size of active portion 620A increases as the second noise level increases and the color of the active portion 620A changes relative to a second noise level threshold. In some embodiments, the size of the active portion 620A includes one or more visually emphasized units (e.g., bubbles, bars, blocks) that are part of one or more units (e.g., the bubbles, bars, blocks) making up the noise meter indicator 620. In some embodiments, each emphasized unit in active portion 620A represents a predetermined number of decibels (e.g., one unit equals 10 dB of noise). In some embodiments, the first noise level threshold and the second noise level threshold are the same noise level (e.g., 86 dB).

The noise levels (e.g., values, amplitudes) indicated by the appearance of noise level indicator 618, noise meter indicator 620, and noise status indicator 622A (e.g., as described below), are updated in response to watch 600B determining one or more noise levels based on received noise data (e.g., the indications update as ambient/environmental noise levels are continuously determined or measured by watch 600B). In some embodiments, noise levels are measured or detected by a device external to watch 600B (e.g., device 600B receives data representing a current noise level from a remote device communicatively coupled with device 600B).

Figure 6D:
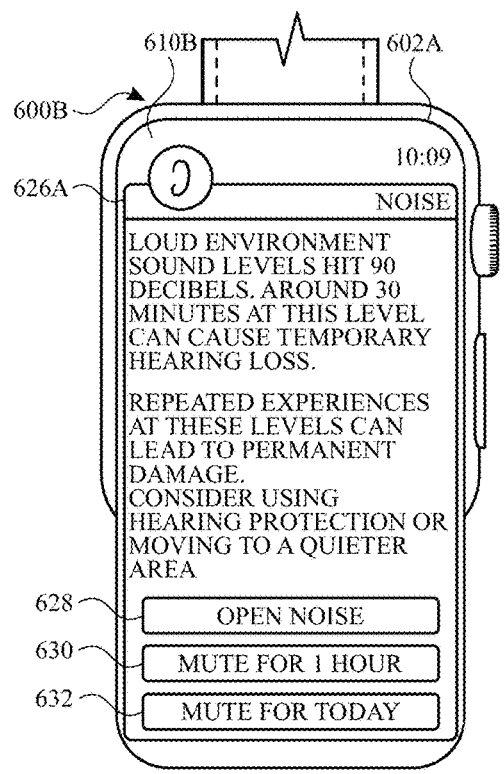

As depicted in FIG. 6D, subsequent to a determination that a noise level (e.g., environmental sound level) exceeds a notification sound level threshold (e.g., 80 dB or 86 dB) for a period of time (e.g., a predetermined amount of time, 1-second, or 3-minutes) and that a sound reduction device (e.g., headphones 600A, earbuds, headphones, etc.) is not being used and/or is not actively producing a sound reduction effect, device 600B displays noise notification user interface 610B including noise notification 626A (e.g., a noise level summary). Noise notification user interface 610B includes an explanation of what constitutes a loud environment, an explanation of the damage to hearing that can be done from exposure to the loud environment, and suggestions for limiting exposure to the loud environment (e.g., "considering using hearing protection"). Noise notification 626A includes portions that extend beyond noise notification user interface 610B displayed on display 602A and that are accessed in response to device 600B receiving user inputs at depressible input mechanism 604 (e.g., a scroll input). In response to receiving the inputs, device 600B displays additional portions of noise notification 626A of noise notification user interface 610B as depicted in FIG. 6D.

As depicted in FIG. 6D, noise notification 626A of noise notification user interface 610A includes noise application affordance 628 for launching the noise application, mute affordances 630 and 632 for suppressing display of subsequent noise notifications (e.g., display of noise notification user interface 610B) for a specified time periods (e.g., 1-hour and the remainder of the day). In some embodiments, in response to receiving a user input (e.g., a tap) that is not on affordance 628, 630, or 632, device 600B displays (e.g., re-displays) noise user interface 610A. In some embodiments, in response to receiving a user input selecting one of the mute affordances 630 and 632 or a dismiss affordance, device 600B displays (e.g., re-displays) user interface 608A or another user interface on display 602A. In some embodiments, selection of one of the mute affordances 630 and 632 causes device 600B to suppress (e.g., to forgo displaying noise notification user interface 610B despite a notification triggering condition being detected by device 600B) subsequent notifications for a predetermined auto-suppression period (e.g., time periods corresponding to the time periods displayed at mute affordances 630 and 632, 1-hour, today, etc.). In some embodiments, notification user interface 610B includes a graphical indication of a noise exposure level (e.g. noise meter indicator 620).

Figure 6E:
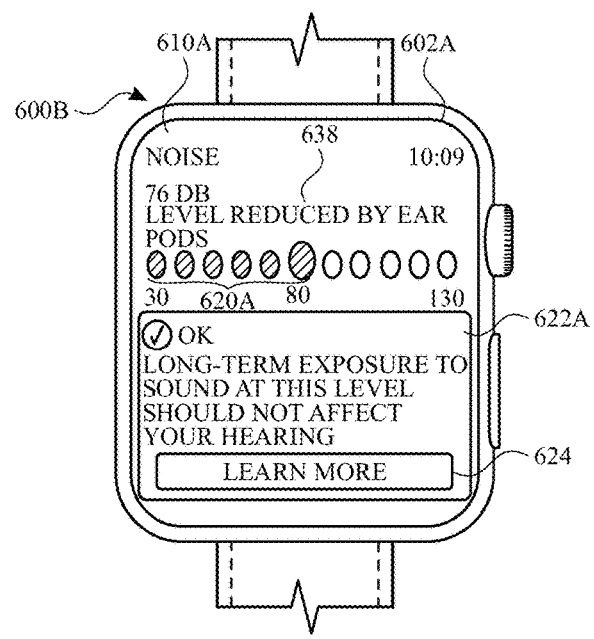

FIG. 6E depicts noise user interface 610A after the user has enabled sound reduction function of headphones 600A, while remaining in the same environment with a 90 dB ambient noise level. User interface 610A includes sound reduction indicator 638 (e.g., "level reduced by ear pods") that informs the user that headphones 600A ("EAR PODS") are reducing the ambient noise level. FIG. 6E further depicts that the environmental sound level is being reduced to a perceived noise level (e.g., a noise level experienced by a user of the sound reduction device (e.g., headphones 600A)), as indicated by noise level indicator 618 to be 76 dB. User noise interface 610A further includes selectable option 624, which displays an indication that the perceived sound level is safe (e.g., "Long term exposure to sound at this level should not affect your hearing").

Figure 6F:
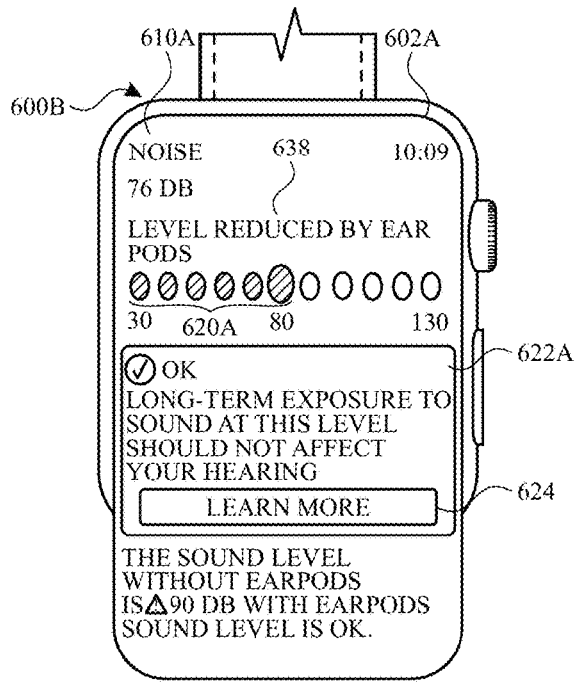

FIG. 6F depicts user interface 610A while the environmental sound level is being actively reduced by headphones 600A to a perceived noise level indicated by noise level indicator 618 to be 76 dB. Noise status indicator 622A is shown displayed on user interface 610 and textually and graphically (e.g., check-mark symbol) indicates that long-term exposure to sound at this level (e.g., 76 dB) will not affect the user's hearing. Noise status indicator also includes selectable "Learn More" option 624. In response to receiving a touch input on option 624, the user can scroll the noise status indicator 622A using rotatable and depressible input mechanism 604 to read the additional text illustrated below option 624, which indicates to the user that the sound level without headphones 600A is above a safe level, but that with headphones 600A the sound level is not damaging to the user's hearing.

Figure 6G:
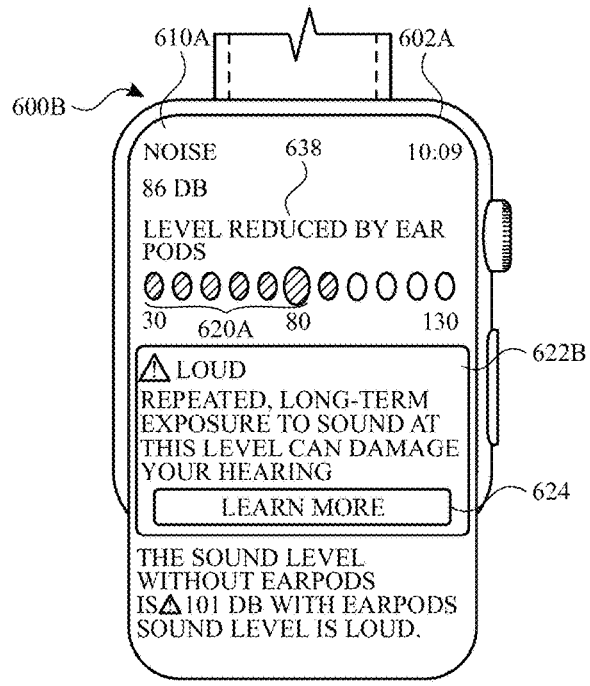

In FIG. 6G, the ambient sound level has increased to 101 dB. FIG. 6G depicts user interface 610A while the environmental sound level (101 dB) is being actively reduced by headphones 600A to a perceived noise level indicated by noise level indicator 618 to be 86 dB. Noise status indicator 622B indicates that repeated long-term exposure to sound at this level (e.g., 86 dB) can damage the user's hearing. In response to receiving a touch input on option 624, the user can scroll the noise status indicator 622A to read the additional text illustrated below option 624, which indicates to the user that the sound level without headphones 600A is above a safe level (e.g., 101 dB), and that with headphones 600A the sound level is still above a safe level.

Figure 6H:
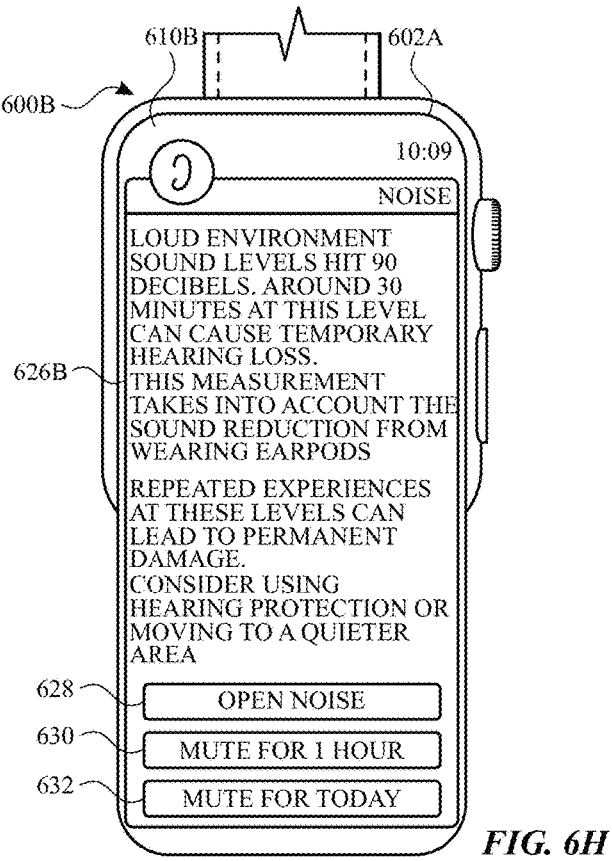

As depicted in FIG. 6H watch 600B displays noise notification user interface 610B including noise notification 626B. Noise notification 626B textually indicates to the user that the user was exposed to sound levels of 90 dB, that hearing loss can result from being exposed to such sound levels, and that the measurement presented takes into account a sound reduction effect from wearing the headphones 600A. Additionally, noise notification 626B provides a textual suggestion to the user to use hearing protection or to move to a less noisy area (e.g., consider using hearing protection or moving to a quieter area).

In FIG. 6H, noise notification user interface 610B includes an explanation of what a loud environment consists of, an explanation of the damage to hearing that can be done from exposure to the loud environment, and suggestions for limiting exposure to the loud environment (e.g., "considering using hearing protection"). Noise notification 626A includes portions that extend beyond noise notification user interface 610B displayed on display 602A and that are accessed in response to device 600B receiving user inputs at depressible input mechanism 604 (e.g., a scroll input). In response to receiving the inputs, device 600B displays additional portions of noise notification 626A of noise notification user interface 610B as depicted in FIG. 6D.

Figure 6I:
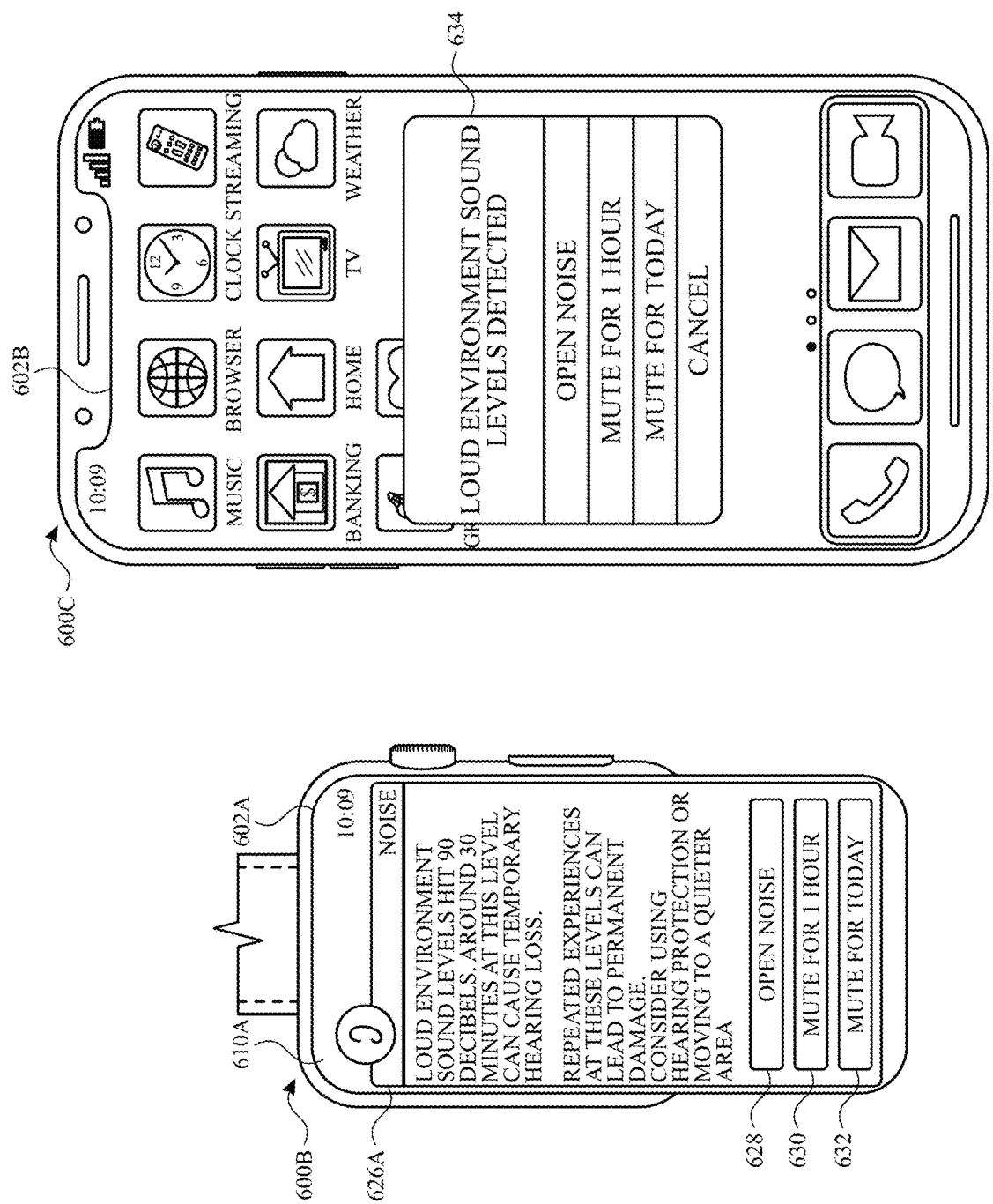

FIG. 6I depicts watch 600B and phone 600C displaying corresponding noise notification 626A and phone noise notification 634 when watch 600B and phone 600C are in communication and a noise notification has been generated by a noise level condition that exceeds the predetermined noise level criteria. In some embodiments, noise notification 626A and phone noise notification 634 are the same. In some embodiments, phone noise notification 634 includes additional information not included with noise notification 626A.

FIG. 7 is a flow diagram illustrating a method 700 for managing and visualizing sound reduction, in accordance with some embodiments. Method 700 is performed at a computer system (e.g., 100, 300, 500, 600B, 600C) (e.g., a smart watch, a smart phone, a personal computer, a laptop, a tablet) that is in communication with a display generation component (e.g., 602A, 602B) (e.g., an integrated display and/or a connected display). In some embodiments, the computer system is tablet, phone, laptop, desktop, a head mounted display ("HMD"), device with a mechanical wheelbase, self-propelled device, smart speaker, personal assistive device, robot, and/or camera. Some operations in method 700 are, optionally, combined, the orders of some operations are, optionally, changed, and some operations are, optionally, omitted.

As described below, method 700 provides an intuitive way for managing and visualizing sound reduction. The method reduces the cognitive burden on a user for managing and visualizing sound reduction, thereby creating a more efficient human-machine interface. For battery-operated computing devices, enabling a user to determine the level of sound they are being exposed to while using a sound reduction device and while not using the sound reduction device faster and more efficiently conserves power and increases the time between battery charges.

The computer system, while a detected environmental noise level (e.g., a currently detected level, previously detected (e.g., recently detected) level, a level over a period of time (e.g., the last 10 seconds, 1 minute, or 5 minutes)) is at a first noise level (e.g., a level measured in decibels; an unmodified, ambient detected noise level), in accordance with a determination that a set of one or more sound reduction criteria are met, displays (702), via the display generation component, a user interface (e.g., 610A) (e.g., an interface of a noise level monitoring application; an interface of a noise level notification) that includes an indication (e.g., 618, 620, 620A) (e.g., a graphical indication and/or a textual indication) that indicates a second noise level that is lower than the first noise level when (e.g., because, as a result of, and/or caused by) a first user (e.g., a user associated with an account logged into the system; a user that is detected via one or more sensors of the system and/or connected to the system) of the computer system is using a sound reduction device (e.g., 600A) (e.g., noise-canceling/noise mitigating headphones, passive earplugs, and/or active earplugs)(e.g., lower based on a detected or estimated amount of noise reduction provided by the sound reduction device). In some embodiments, the environmental noise level is detected by an acoustic sensor (e.g., a microphone) that is in communication with the computer system (e.g., an integrated sensor, a separate sensor connected to the system). In some embodiments, the system is in communication with two or more acoustic sensors that includes an acoustic sensor that detects unmodified, ambient noise and a sensor that detects ambient noise, as modified by the sound reduction device. In some embodiments, the indication also indicates (e.g., graphically or textually) that the second noise level is a modified noise level.

The computer system, while the detected environmental noise level is at the first noise level, in accordance with a determination that the set of one or more sound reduction criteria are not met (e.g., as shown in FIG. 6C), displays (704), via the display generation component, a second user interface (e.g., 610A) that indicates the first noise level (e.g., indicates an unmodified/unreduced noise level) (e.g., 618 and 620A of FIG. 6C). In some embodiments, the second user interface includes one or more graphical elements that are also in the first user interface. Automatically displaying the indication that indicates the first noise level or the second noise level, based on whether the set of criteria are met provides the user with information about whether sound reduction is in effect. Performing an operation when a set of conditions has been met without requiring further user input and providing improved visual feedback both reduce power usage and improve battery life of the system by enabling the user to use the device more quickly and efficiently.

In some embodiments, in accordance with a determination that a set of one or more sound reduction criteria are met (e.g., as shown in FIG. 6E), the first user interface includes an indication (e.g., 638) (e.g., a textual or graphical indication) that the second noise level is based on use of the sound reduction device, and in accordance with a determination that the set of one or more sound reduction criteria are not met, the second user interface does not include the indication that the second noise level is based on use of the sound reduction device. In some embodiments, the second user interface includes an indication that the first noise level is an environmental noise level and/or an unmodified noise level. Including an indication that the second noise level is based on use of the sound reduction device when certain criteria are met allows the user to quickly recognize when the indication takes into account sound reduction. Performing an operation when a set of conditions has been met without requiring further user input and providing improved visual feedback both reduce power usage and improve battery life of the system by enabling the user to use the device more quickly and efficiently.

In some embodiments, while displaying the first user interface, the computer system detects that the user of the computer system is no longer using the sound reduction device, and in response to detecting that the user of the computer system is no longer using the sound reduction device, the display generation component displays an indication (e.g., 626A) (e.g., a textual (e.g., "Sound reduction is not active) or graphical indication) that sound reduction is not active. In some embodiments, the computer system detects that the set of one or more sound reduction criteria are no longer met. In some embodiments, the display generation component transitions to display the second user interface. Automatically displaying an indication that sound reduction is not active when certain conditions are met, automatically provides the user with visual feedback of the change in sound reduction status. Performing an operation when a set of conditions has been met without requiring further user input and providing improved visual feedback both reduce power usage and improve battery life of the system by enabling the user to use the device more quickly and efficiently.

In some embodiments, while displaying the first user interface, the computer system detects that the set of one or more sound reduction criteria are no longer met, and in response to detecting that the set of one or more sound reduction criteria are no longer met, replaces the first user interface (e.g., 610A of FIG. 6C) with the second user interface (e.g., 610A of FIG. 6E). Automatically updating the indication from the second noise level to the first noise level when the set of one or more criteria are no longer met, automatically provides the user with visual feedback of the change in sound reduction status. Performing an operation when a set of conditions has been met without requiring further user input and providing improved visual feedback both reduce power usage and improve battery life of the system by enabling the user to use the device more quickly and efficiently.

In some embodiments, in accordance with a determination that the set of one or more sound reduction criteria are met, the first user interface further indicates (e.g., in addition to indicating the second sound level) the first noise level (e.g., the indication indicates the first noise level and the second noise level) (e.g., as seen in FIG. 6G ("the sound level without Ear Pods is 101 dB). Automatically including an indication of the first noise level (e.g., the environmental noise level) and the second noise level (e.g., the reduced noise level) when criteria are met provides the user with feedback as to both noise levels, allowing the user to compare them. Performing an operation when a set of conditions has been met without requiring further user input and providing improved visual feedback both reduce power usage and improve battery life of the system by enabling the user to use the device more quickly and efficiently.

In some embodiments, in accordance with a determination that the set of one or more sound reduction criteria are met and in accordance with a determination that the second noise level exceeds a first noise level threshold (e.g., a safe noise level threshold), the first user interface further indicates (e.g., via 622B, 626A, and 626B) (e.g., textually, graphically) that the noise level threshold has been exceeded (e.g., "around 30 min at this level can cause temporary hearing loss."). Automatically including an indication that a noise level threshold has been exceeded when criteria are met provides the user with feedback as to both noise levels, allowing the user to compare them. Performing an operation when a set of conditions has been met without requiring further user input and providing improved visual feedback both reduce power usage and improve battery life of the system by enabling the user to use the device more quickly and efficiently.

In some embodiments, in accordance with a determination that the set of one or more sound reduction criteria are met and in accordance with a determination that the second noise level exceeds a second noise level threshold (e.g., a safe noise level threshold; a threshold that is the same or different from the first noise level threshold), including, in the first user interface a first selectable graphical object (e.g., 624), that when selected, causes display (e.g., launches the application) of a user interface (e.g., 610B) of a hearing-related application (e.g., 614) (e.g., an application that includes information and/or one or more functions related to monitoring hearing), and a second selectable graphical object (e.g., 628, 630, 632), that when selected, initiates a process to suppress one or more noise-related notifications (e.g., 622B) (e.g., future notifications that would be issued, if not suppressed, when one or more noise-related criteria are met (e.g., when a safe noise level is exceeded)). In some embodiments, the user interface further includes an indication (e.g., textual or graphical) to take steps to reduce the noise level (e.g., to move to a less noisy location). Automatically providing selectable options to open a hearing-related application and to manage noise-related notifications when certain criteria are met provides the user relevant functionality and feedback as to the criteria being met. Performing an operation when a set of conditions has been met without requiring further user input and providing improved visual feedback both reduce power usage and improve battery life of the system by enabling the user to use the device more quickly and efficiently.

In some embodiments, while the first noise level (e.g., the environmental noise level) is above a third noise threshold (e.g., a safe noise level threshold; a threshold that is the same or different from the first or second noise level thresholds): in accordance with a determination that the set of one or more sound reduction criteria are not met, including, in the second user interface, an indication (e.g., 622A) (e.g., a graphical or textual indication) that the first noise level (e.g., the environmental noise level) has exceeded the third noise threshold, and in accordance with a determination that the set of one or more sound reduction criteria are met and a determination that the second noise level (e.g., the noise level as reduced by a sound reduction effect) is not above the third noise threshold, forgoing including, in the first user interface, an indication (e.g., 622B) that the second noise level has exceeded the third noise threshold. In some embodiments, in accordance with a determination that the set of one or more sound reduction criteria are met and a determination that the second noise level is above the third noise threshold, including, in the first user interface, an indication that the second noise level has exceeded the third noise threshold. Automatically including or not including indications that a noise level (e.g., the first or second) is above a threshold noise level provides the user with relevant feedback, when certain conditions are met. Performing an operation when a set of conditions has been met without requiring further user input and providing improved visual feedback both reduce power usage and improve battery life of the system by enabling the user to use the device more quickly and efficiently.

In some embodiments, in accordance with a determination that the set of one or more sound notification criteria are met: issuing a first notification (e.g., 626A) (e.g., a visual, audio, and/or haptic notification) based on the set of one or more sound notification criteria being met (e.g., a notification that a safe sound level threshold has been exceeded), and initiating a process (e.g., by transmitting data and/or instructions to the external computer system) to cause an external computer system (e.g., 600C) that is in communication with the computer system to issue a second notification (e.g., 634) (e.g., a visual, audio, and/or haptic notification) based on the set of one or more sound notification criteria being met (e.g., a notification that a safe sound level threshold has been exceeded). In some embodiments, the set of one or more sound notification criteria include a criterion that is met when the first and/or the second noise levels exceed a fourth noise threshold (e.g., a safe noise level threshold; a threshold that is the same or different from the first, second, and/or third noise level thresholds)). Automatically causing notifications to be automatically issued when criteria are met provides the user with feedback as to a potentially relevant event. Performing an operation when a set of conditions has been met without requiring further user input and providing improved visual feedback both reduce power usage and improve battery life of the system by enabling the user to use the device more quickly and efficiently.

In some embodiments, the computer system is in communication with one or more audio sensors (e.g., 606) (e.g., microphones), the first and second noise levels are detected via the one or more audio sensors, and the sound reduction device is an external sound reduction device (e.g., 600A) (e.g., external noise-canceling/noise mitigating headphones, passive earplugs, and/or active earplugs).

Note that details of the processes described above with respect to method 700 (e.g., FIG. 7) are also applicable in an analogous manner to the methods described below. For example, methods 900 and 1000 optionally includes one or more of the characteristics of the various methods described above with reference to method 700. For example, the environmental sound level graph with a sound reduction option elements of method 900 and the sound reduction graph elements of method 1000 can be combined with the indication of a noise level a user is exposed to while using a sound reduction device or not using a sound reduction device elements of method 700 within one or more user interfaces of one or more of user devices 600B and 600C. For brevity, these details are not repeated below.

FIGS. 8A-8H depict device 800 displaying user interfaces (e.g., user interface 802A-802H) on display 602B for accessing and displaying noise exposure data for a user, including environmental noise data (e.g., the noise level of the environment the user is in) and sound reduction noise data (e.g., the noise level of the environment the user is in reduced by a sound reduction effect produced by a sound reduction device being worn by the user).

Figure 8A:
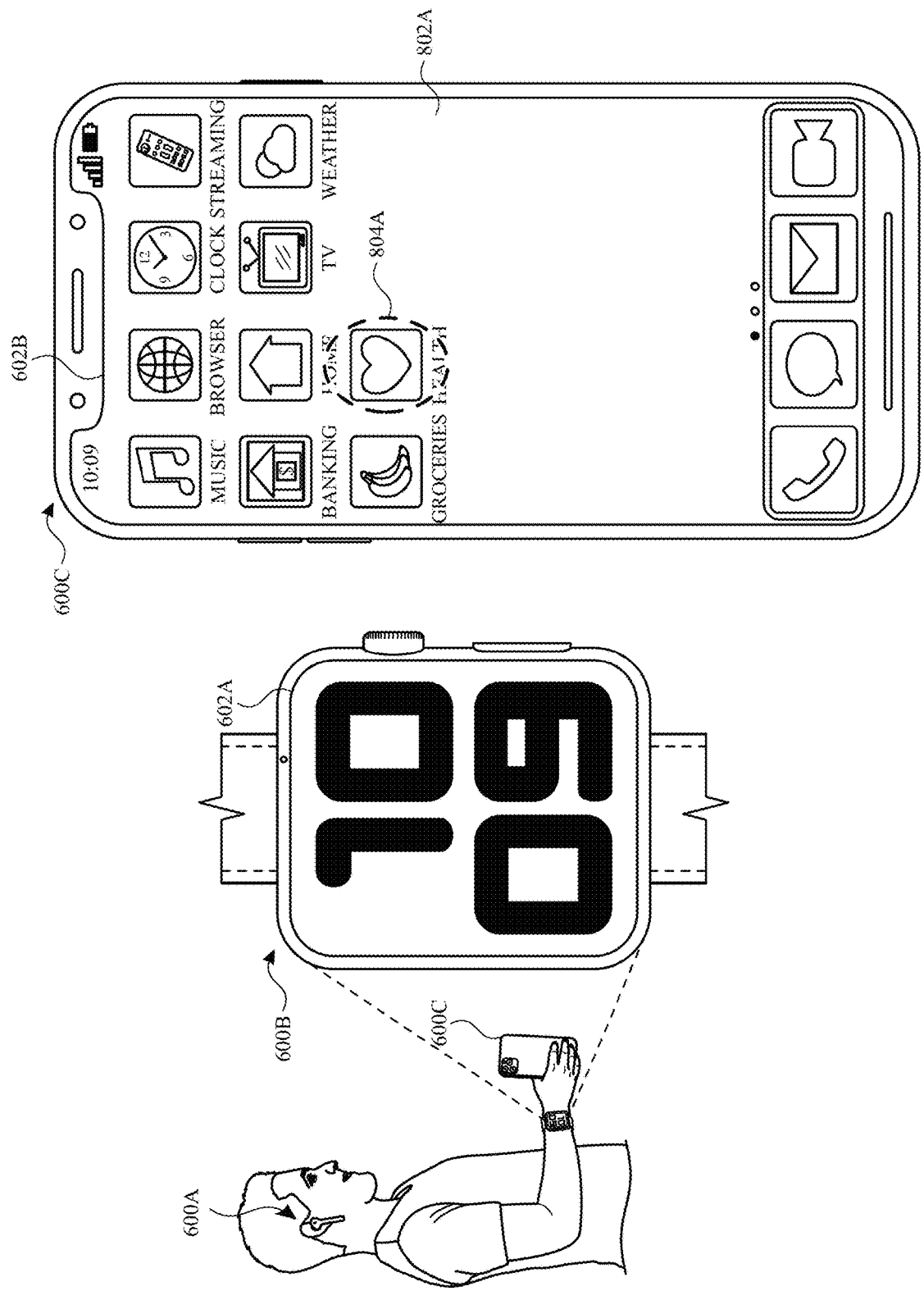
FIGS. 8A-8B illustrate exemplary user components and user interfaces of personal electronic devices in accordance with some embodiments.

FIG. 8A illustrates the user who is wearing headphones 600A, watch 600B, and using phone 600C, similar to what was shown in FIG. 6A. In FIG. 8A, phone 600C is displaying a home screen 802A. As depicted in FIG. 8A, phone 600C receives input 804A from the user at the health affordance illustrated on home screen 802A, and in response, displays health user interface 802B, as shown in FIG. 8B.

Figure 8C:
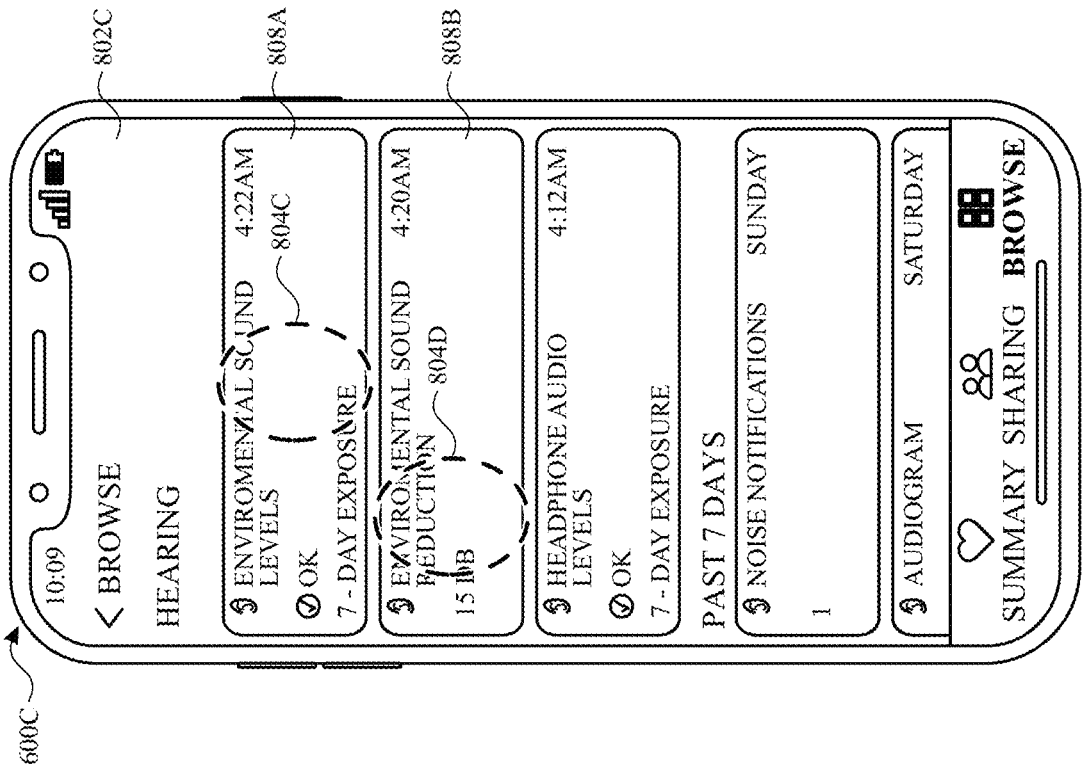
Figure 8B:
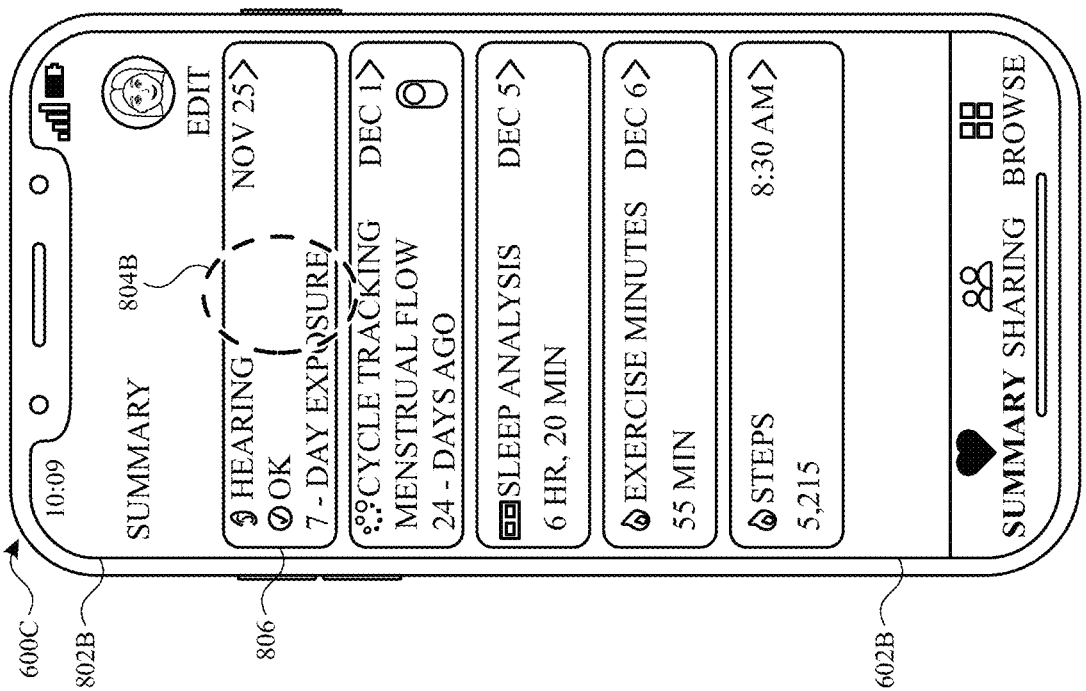
Figure 9B:
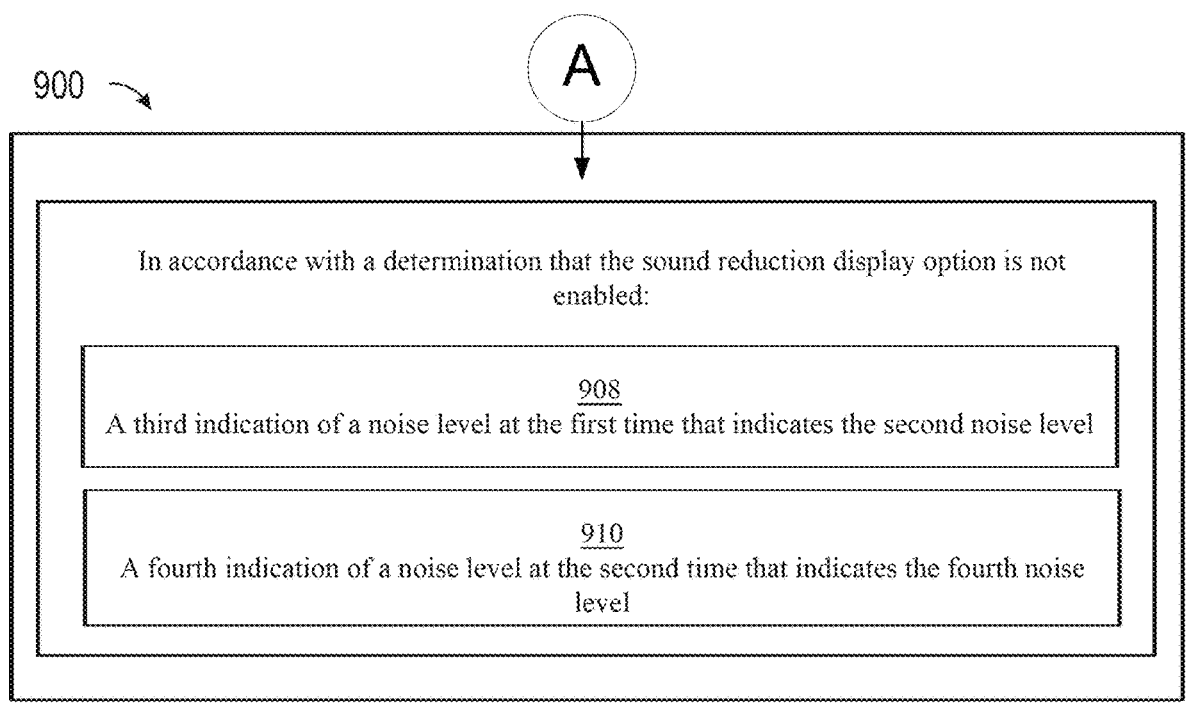

FIG. 8B illustrates health user interface 802B displayed on display 602B of phone 600C for accessing user health data. FIG. 8B further depicts phone 600C receiving input 804B at hearing affordance 806. Upon detecting this input, phone 600C displays hearing user interface 802C as depicted in FIG. 8C.

FIG. 8C depicts phone 600C displaying hearing user interface 802C on display 602B, in response to the input received at hearing affordance 806. Hearing user interface 802C includes various affordances for accessing, displaying, and manipulating noise data (e.g., environmental noise data and sound reduction noise data) over a selectable period of time (e.g., day, week, month, year, etc.). FIG. 8C depicts phone 600C receiving user input 804C at environmental sound levels affordance 808A and receiving user input 804D at environmental sound reduction affordance 808B. In response to detecting user input 804C, phone 600C displays sound level user interfaces 802D and 802E illustrated in FIGS. 8D-8E. In response to detecting user input 804D, phone 600C displays sound reduction user interfaces 802F-802H illustrated in FIGS. 8F-8H.

FIGS. 8D-8E depict sound level exposure user interfaces 802D and 802E, respectively, including graph 814A and 814B displaying noise exposure data (e.g., amplitudes or levels of noise that the user has been exposed to) for a time period that is selectable via the time period icons 810 (e.g., hour, day, week, month, 6 months, year).

As depicted in FIG. 8D, noise exposure data associated with a week is selected via user input (e.g., a tap) on the "W" of the time period icons 810. In response to detecting the selection of the "W", phone 600C bolds the "W" icon and updates graph 814A to display sound level exposure with sound reduction for the user for a period of a week in order to provide a visual indication of the noise exposure data determined by watch 600B.

As depicted in FIG. 8D, exposure indication 816A indicates, graphically (e.g., via the "check mark") and textually (e.g., "Exposure OK") that the sound level exposure for the user of the phone 600C is at an exposure level that is considered to not be harmful (e.g., below 80 dB, etc.) for the selected period (e.g., week). Sound level exposure user interface 802D further includes various affordances for manipulating sound exposure data displayed by graph 814A (e.g., exposure with sound reduction affordance 812A). FIG. 8D depicts "Exposure with Sound Reduction" affordance 812A as bolded, indicating that affordance 812A is currently selected (e.g., selected via user input). In response to the selection of affordance 812A, graph 814A displays sound level exposure for the user that is the result of a sound reduction effect via headphones 600A (e.g., a sound level exposure that is less than the environmental sound level of the environment that the user was present in at the relevant time).

As depicted in FIG. 8D, graph 814A displays the time along the X-axis (e.g., the day, "SUN", "MON", etc.) and decibels along the Y-axis (e.g., 0 to 100 dB). A plot of the measured sound level exposures for each day of the week is displayed on graph 814A as a visual indicator of the sound level exposure for each day of the period for the user. Additionally, as depicted in FIG. 8D, a straight line extending parallel to the X-axis of graph 814A corresponds to an average sound level exposure with sound reduction (e.g., 76 dB) for the time period (e.g., week). In some embodiments, the line corresponds to a median of the sound level exposure with sound reduction.

As depicted in FIG. 8D, the various affordances for manipulating sound exposure data further include Exposure with Sound Reduction affordance 812B, Daily Averages affordance 812C, Latest Affordance 812D, Range affordance 812E, and Noise Notifications affordance 812F. As shown in FIG. 8E, selecting the Exposure with Sound Reduction affordance 812B results in graph 814B displaying a graphical representation of the level of sound exposure that the user of the phone 600C would have been exposed to if the sound reduction effect of the headphones 600A was not enabled. Daily Averages affordance 812C displays the daily averages for the sound level exposure that the user is exposed to for the period. In some embodiments, Daily Averages affordance 812C displays a range of daily sound level exposure averages including the lowest daily average and the highest daily average sound level exposure for the user. In some embodiments, in response to selection of Daily Averages affordance 812C, additional information related to the daily averages of the sound level exposure is displayed on display 602B.

As depicted in FIG. 8D, Latest Affordance 812D displays the latest noise level data and the time that the noise level data was determined (e.g., "4:25 AM 52 dB). In some embodiments, in response to selection of Latest Affordance 812D, phone 600C displays additional information related to the latest sound level exposure data. Range affordance 812E displays a range of sound levels (e.g., 46-102 dB) that the user has been exposed to during the selected period (e.g., week). In some embodiments, in response to selection of Range affordance 812E, phone 600C displays additional information related to the range of sound level exposure data. Noise Notifications affordance 812F displays the number of noise notifications (e.g., 1) that have been generated during the selected time period (e.g., week). In some embodiments, in response to selection of Noise Notifications affordance 812F, phone 600C displays additional information related to the noise notifications (e.g., historical notification data, notification setup, etc.).

As depicted in FIG. 8E, the noise exposure data associated with the week remains selected. In response to selection of Exposure without Sound Reduction affordance 812B, graph 814B displays sound level exposure without sound reduction (e.g., environmental sound level) for the user for the period of the week in order to provide a visual indication of the noise exposure data determined by the wearable user device (e.g., watch) 600B.

As depicted in FIG. 8E, exposure indication 816B indicates, graphically (e.g., via the triangle with an exclamation mark symbol) and textually (e.g., "Exposure Loud") that the sound level exposure for the user of phone 600C is at an exposure level that is considered to be loud (e.g., potentially harmful to the user, above 80 dB, etc.) for the selected period (e.g., week). Due to the selection of affordance 812B, graph 814B displays sound level exposure for the user for the week that corresponds to the environmental sound level for the environment the user was in throughout the week (e.g., the sound level exposure does not take into account a sound reduction effect via headphones 600A for the time period). As also depicted in FIG. 8E, the straight line illustrated on graph 814B corresponds to an average sound level exposure without sound reduction (e.g., 82 dB) for the time period (e.g., week) for the user of phone 600C.

Figure 8G:
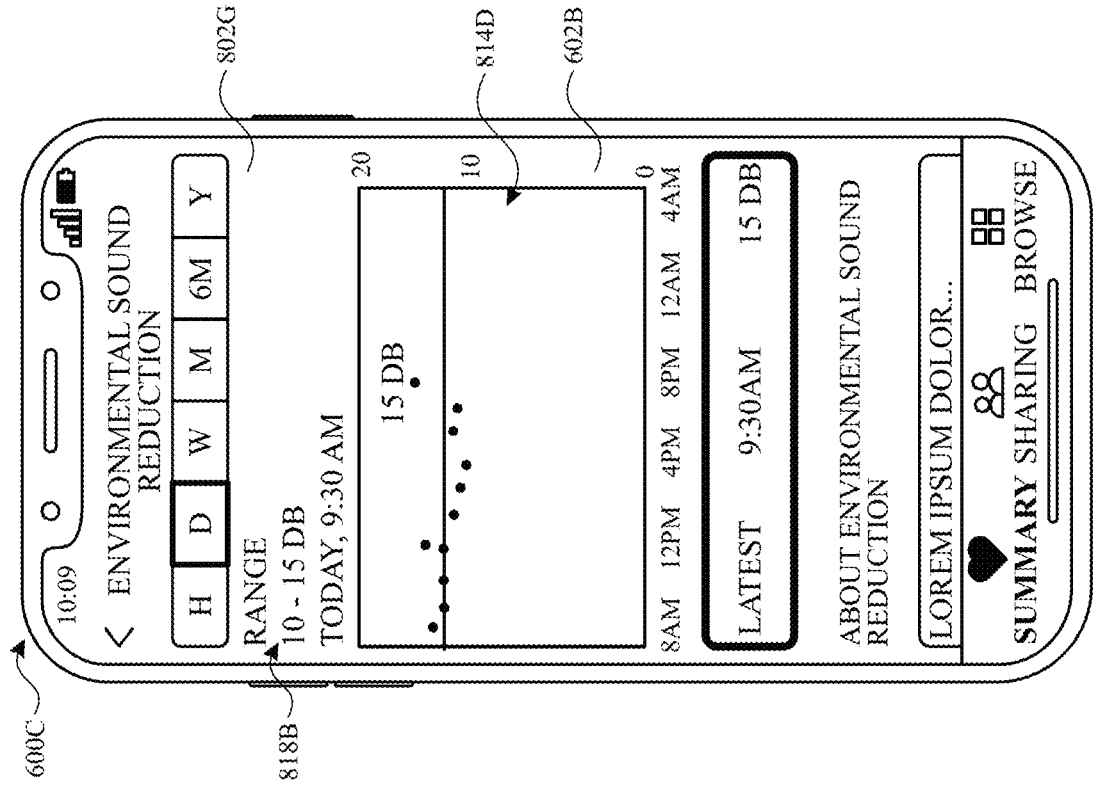
FIGS. 8F-8H illustrate exemplary user interfaces for monitoring sound reduction levels in accordance with some embodiments.
Figure 8F:
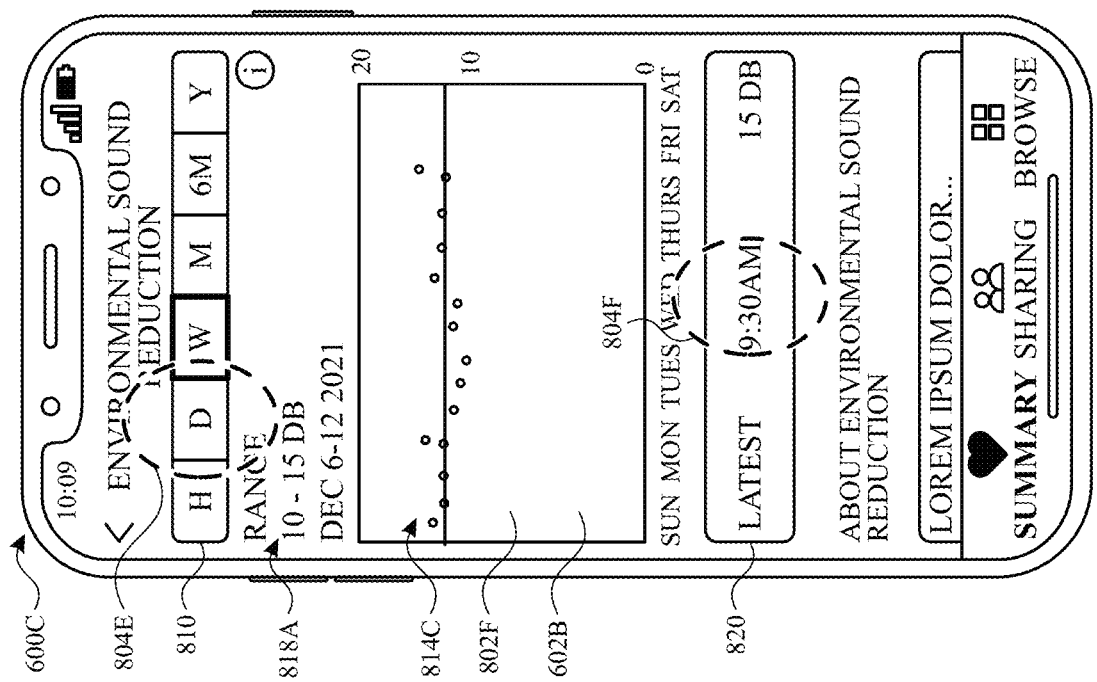
Figure 8H:
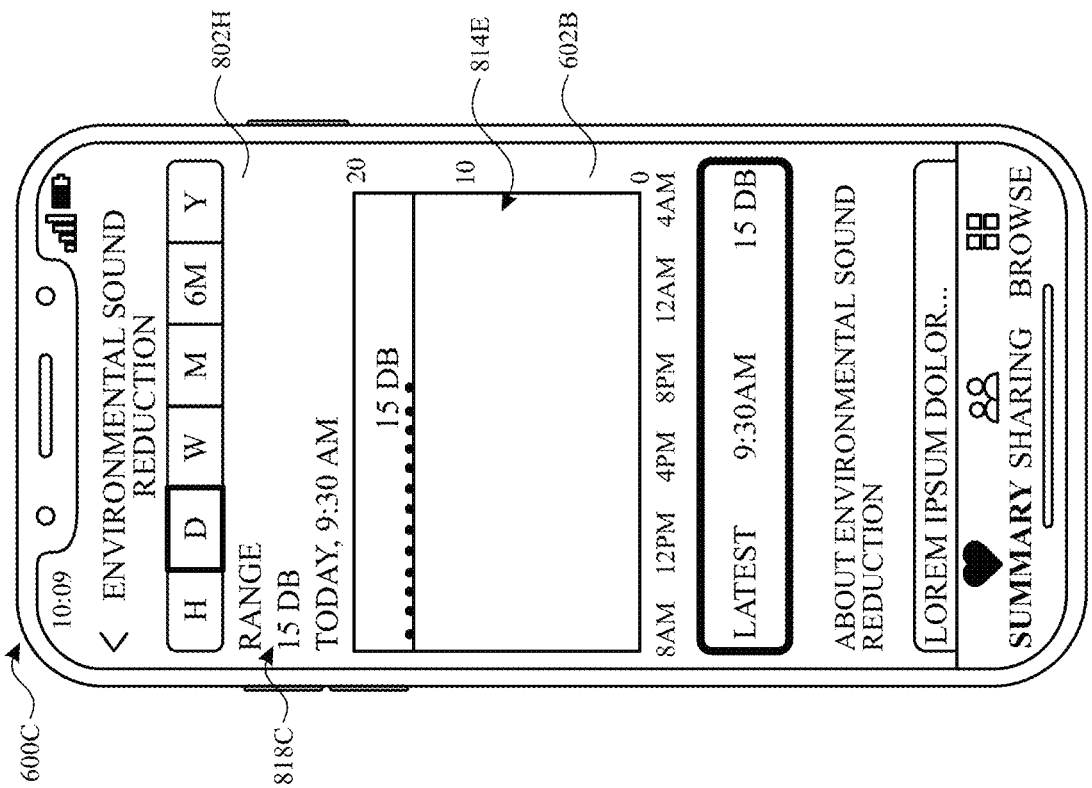

FIGS. 8F-8H depict sound reduction effect user interfaces 802F-802H, respectively, including graphs 814C, 814D, and 814E which display sound reduction effect data (e.g., amplitudes or levels of sound reduction generated by earphones 600A) for a time period that is selectable via time period icons 810 (e.g., hour, day, week, month, 6 months, year, etc.).

As depicted in FIG. 8F, sound reduction effect data associated with a week is displayed in graph 814C of sound reduction user interface 802F. Graph 814C displays the time along the X-axis (e.g., the day, "SUN", "MON", etc.) and decibels along the Y-axis (e.g., 0 to 20 dB). Points displayed on graph 814C represent an active (e.g., variable in response to environmental sound levels in order to attempt to maintain a sound level perceived by the user of headphones 600A) sound reduction effect (e.g., the amount of sound cancellation produced by earphones 600A) for each day of the week of the period for the user wearing earphones 600A. Additionally, as depicted in FIG. 8F, a straight line extending parallel to the X-axis of graph 814C corresponds to an average sound reduction effect (e.g., 10 dB) for the time period (e.g., week). In some embodiments, the line corresponds to a median of the sound reduction effect.

As depicted in FIG. 8F, graph 814A displays the time along the X-axis (e.g., the day, "SUN", "MON", etc.) and decibels along the Y-axis (e.g., 0 to 100 dB). A plot of the measured sound level exposures for each day of the week is displayed on graph 814A as a visual indicator of the sound level exposure for each day of the period for the user. Additionally, as depicted in FIG. 8D, a straight line extending parallel to the X-axis of graph 814A corresponds to an average sound level exposure with sound reduction (e.g., 76 dB) for the time period (e.g., week). In some embodiments, the line corresponds to a median of the sound level exposure with sound reduction. As depicted in FIG. 8F, range indicator 818A displays a range of sound reduction effects (e.g., an amount of sound cancellation produced by earphones 600A) that the user has experienced via earphones 600A during the selected (e.g., week).

FIG. 8F depicts receiving user input 804E (e.g., a tap) on the "D" (e.g., day) representation of time period icons 810 (e.g., hour, day, week, month, 6 months, year, etc.) and receiving user input 804F on "Latest" affordance 820. As depicted in FIG. 8G, in response to selection of the "D" icon of sound reduction user interface 802G, the "D" icon is bolded and graph 814D displays sound reduction effects from earphones 600A for a single day. As also depicted in FIG. 8G, in response to selection of "Latest" affordance 820, the chronologically most recent sound reduction effect data point on graph 814D is bolded.

As depicted in FIG. 8G, active sound reduction effect data associated with a day is displayed in graph 814D. Range indicator 818B displays a range of sound reduction effects that the user has experienced via earphones 600A during the selected period (e.g., day). Graph 814D includes a textual summary of the points displayed on graph 814D represent an active sound reduction effect determined at a time in four hour intervals throughout a day. Additionally, as depicted in FIG. 8G, a straight line extending parallel to the X-axis of graph 814D corresponds to an average sound reduction effect (e.g., 10 dB) for the time period (e.g., day). In some embodiments, the line corresponds to a median of the sound reduction effect.

As depicted in FIG. 8H, constant sound reduction effect (e.g., the sound reduction effect of earphones 600A is a constant amount that does not vary with environmental sound levels where the user and/or watch 600B are located) data associated with a day is displayed in graph 814E. Points displayed on graph 814E represent a constant sound reduction effect determined at a time at four hour intervals throughout a day.

FIGS. 9A-9B are a flow diagram illustrating a method 900 for managing and visualizing sound reduction, in accordance with some embodiments. Method 900 is performed at a computer system (e.g., 100, 300, 500, 600B, 600C) (e.g., a smart watch, a smart phone, a personal computer, a laptop, a tablet) that is in communication with a display generation component (e.g., 602A, 602B) (e.g., an integrated display and/or a connected display). In some embodiments, the computer system is tablet, phone, laptop, desktop, a head mounted display ("HMD"), device with a mechanical wheelbase, self-propelled device, smart speaker, personal assistive device, robot, and/or camera. Some operations in method 900 are, optionally, combined, the orders of some operations are, optionally, changed, and some operations are, optionally, omitted.

The computer system displays (902), via the display generation component, a representation (e.g., 814A, 814B) (e.g., a graph, a chart) of a noise level (e.g., the noise level in the environment that the system and/or a user of the system was in at the time) at a plurality of different times (e.g., different times in a given day, different days of the week, different weeks in a year).

The representation includes, in accordance with a determination that a sound reduction display option (e.g., 812A) is enabled (e.g., enabled via user input on an affordance): a first indication of a noise level at a first time (e.g., 810) (e.g., a first day (e.g., a Monday)) of the plurality of different times that indicates (904), in accordance with a determination that sound reduction was in effect at the first time (e.g., that the user (e.g., a user associated with an account logged into the system; a user that is detected via one or more sensors of the system and/or connected to the system) of the computer system was using a sound reduction device (e.g., noise-canceling/noise mitigating headphones, passive earplugs, and/or active earplugs)), a first noise level, wherein the first noise level is based on an environmental noise level at the first time (e.g., a detected level, previously detected (e.g., recently detected) level, or a level over a period of time (e.g., the last 10 seconds, 1 minute, or 5 minutes) that are associated with the first time; an average, median, maximum, minimum or modal noise level over a period of time that is the first time (e.g., a day)) and a first sound reduction effect that was in effect at the first time, and in accordance with a determination that sound reduction was not in effect at the first time, a second noise level (e.g., an unmodified environmental noise level) that is greater than the first noise level, wherein the second noise level is based (e.g., only, solely) on the environmental noise level at the first time, a second indication of a noise level at a second time (e.g., a second day (e.g., a Tuesday)) of the plurality of different times that is different from the first time and that indicates (906), in accordance with a determination that sound reduction was in effect at the second time, a third noise level, wherein the third noise level is based on an environmental noise level at the second time and a second sound reduction effect that was in effect at the second time, and in accordance with a determination that sound reduction was not in effect at the second time, a fourth noise level that is greater than the third noise level, wherein the fourth noise level is based (e.g., only, solely) on the environmental noise level at the second time. In some embodiments, the sound reduction option is a toggle affordance that is toggled between being enabled and not enabled. In some embodiments, the sound reduction option is a selectable option that is separate from an option for not displaying sound reduction. In some embodiments, the second noise level is based on the environmental noise level at the first time and is not based on the first sound reduction effect that was in effect at the first time. In some embodiments, the second noise level is not based on any sound reduction effect that was in effect at the first time. In some embodiments, the fourth noise level is based on the environmental noise level at the second time and is not based on the second sound reduction effect that was in effect at the first time. In some embodiments, the fourth noise level is based on the environmental noise level at the second time and is not based on any sound reduction effect that was in effect at the first time.

The representation includes, in accordance with a determination that the sound reduction display option is not enabled (e.g., via selection of 812B) (e.g., is disabled or that a display without sound reduction option is enabled), a third indication of a noise level at the first time that indicates (908) the second noise level, and a fourth indication of a noise level at the second time that indicates (910) the fourth noise level. In some embodiments, the third indication of the noise level at the first time indicates the second level of environmental noise regardless of whether sound reduction was in effect at the first time. In some embodiments, the fourth indication of the noise level at the second time that indicates the fourth level of environmental noise regardless of whether sound reduction was in effect at the second time. Providing a representation of noise data that is based on a sound reduction effect or not based on that effect, depending on whether an option is enabled, automatically provides the user with improved feedback as to detected noise levels at the plurality of times. Providing improved visual feedback reduces power usage and improves battery life of the system by enabling the user to use the device more quickly and efficiently.

In some embodiments, while the sound reduction display option is not enabled, the computer system receives a first user input (e.g., as shown by 812A in FIG. 8D) (e.g., a tap and/or a mouse click on an affordance, an audio input) corresponding to a request to enable the sound reduction display option, and in response to receiving the first user input, updates the representation of the noise level at the plurality of different times to include the first indication of the noise level at the first time and the second indication of the noise level at the second time. In some embodiments, the computer system ceases to include the third indication of the noise level at the first time and the fourth indication of the noise level at the second time in the representation. Providing a representation of noise data that is based on a sound reduction effect provides the user with improved feedback as to detected noise levels and the sound reduction effect at the plurality of times. Providing improved visual feedback reduces power usage and improves battery life of the system by enabling the user to use the device more quickly and efficiently.

In some embodiments, while the sound reduction display option is enabled, the computer system receives a second user input (e.g., a tap and/or a mouse click on an affordance, an audio input) corresponding to a request to disable the sound reduction display option, and in response to receiving the second user input, updates the representation of the noise level (e.g., 814B) at the plurality of different times to include the third indication of the noise level at the first time and the fourth indication of the noise level at the second time. In some embodiments, the computer system ceases to include the first indication of the noise level at the first time and the second indication of the noise level at the second time in the representation. Providing a representation of noise data that is not based on a sound reduction effect provides the user with improved feedback as to detected environmental noise levels at the plurality of times. Providing improved visual feedback reduces power usage and improves battery life of the system by enabling the user to use the device more quickly and efficiently.

In some embodiments, the computer system is in communication with one or more audio sensors (e.g., 606) (e.g., microphones), the noise levels at the plurality of different times are detected via the one or more audio sensors, and the sound reduction device is an external sound reduction device (e.g., 600A) (e.g., external noise-canceling/noise mitigating headphones, passive earplugs, and/or active earplugs).

In some embodiments, the one or more audio sensors are integrated into an external computer system (e.g., 600B) (e.g., a smart watch) that is in communication with the computer system, and the representation of the noise level at the plurality of different times is included in a user interface (e.g., 802D, 803E) of a health application (e.g., 614) that generates (e.g., manages, includes) a plurality of user interfaces based on biometric data of a user of the computer system. Including the representation of the noise level at a plurality of different times as part of a health application provides the user with feedback as to various biometric parameters relevant to the user's health. Providing improved visual feedback reduces power usage and improves battery life of the system by enabling the user to use the device more quickly and efficiently.

In some embodiments, while the sound reduction display option is not enabled, the third indication is a graphical indication that varies along a first axis (e.g., a vertical axis) to indicate a range of environmental noise levels at the first time (e.g., range of noise levels detected during a specific hour, day, or week), the fourth indication is a graphical indication that varies along the first axis to indicate a range of environmental noise levels at the second time, the third indication and fourth indication are arranged along a second axis, different from the first axis (e.g., a horizontal axis), and the representation (e.g., 814B) of the noise level at the plurality of different times includes a first average noise level indication (e.g., a horizontal line that varies in the vertical direction to indicate the average noise level over the plurality of times) that extends along the second axis and that indicates the average environmental noise level during the plurality of different times. In some embodiments, the first, and/or second indications is a graphical indication that varies along a first axis to indicate a range of environmental noise levels at the first time. Providing indicators of the range of noise levels at various times as well as the average noise levels at those times provides the user with feedback as to the detected noise levels. Providing improved visual feedback reduces power usage and improves battery life of the system by enabling the user to use the device more quickly and efficiently.

In some embodiments, while the sound reduction display option is enabled, the first indication is a graphical indication and includes a first subportion that varies along a third axis (e.g., a vertical axis) and indicates a range of the noise level at the first time, as reduced by the first sound reduction effect at the first time (e.g., a range of the modified/reduced noise level detected during the first time), the second indication is a graphical indication that includes a second subportion that varies along the third axis and indicates a range of the noise level at the second time, as reduced by the second sound reduction effect at the second time (e.g., a range of the modified/reduced noise level detected during the first time), the first indication and second indication are arranged along a fourth axis, different from the third axis (e.g., a horizontal axis), and the representation (e.g., 814A) of the noise level at the plurality of different times includes a second average noise level indication (e.g., a horizontal line that varies in the vertical direction to indicate the average reduced noise level over the plurality of times) that extends along the fourth axis and that indicates the average noise level during the plurality of different times, as reduced by the first sound reduction effect during the plurality of different times. Providing indicators of the range of reduced noise levels at various times as well as the average reduced noise levels at those times provides the user with feedback as to the detected noise levels and the amount of sound reduction. Providing improved visual feedback reduces power usage and improves battery life of the system by enabling the user to use the device more quickly and efficiently.

In some embodiments, the first indication includes a third subportion that varies along the third axis and indicates a range of environmental noise levels at the first time, the second indication includes a fourth subportion that varies along the third axis and indicates a range of environmental noise levels at the second time, and the representation (e.g., 814A) of the noise level at the plurality of different times includes a third average noise level indication (e.g., a horizontal line that varies in the vertical direction to indicate the average reduced noise level over the plurality of times) that extends along the fourth axis and that indicates the average environmental noise level during the plurality of different times. Providing indicators of the range of reduced and environmental noise levels at various times as well as the average reduced and environmental noise levels at those times provides the user with feedback as to the detected noise levels and the amount of sound reduction. Providing improved visual feedback reduces power usage and improves battery life of the system by enabling the user to use the device more quickly and efficiently.

In some embodiments, the determination that sound reduction was in effect at the first time includes a determination that a user of the computer system was wearing (e.g., using) a sound reduction device (e.g., 600A of FIGS. 6A and 8A) (e.g., noise-canceling/noise mitigating headphones, passive earplugs, and/or active earplugs in both cars) for both cars. In some embodiments, using only one headphone, even if sound reduction is enabled for that headphone, results in a determination that sound reduction was not in effect. Displaying indications of reduced sound levels only when both cars are affected by sound reduction automatically provides users with information about the sound levels experienced by either car and provides feedback as to the same. Performing an operation when a set of conditions has been met without requiring further user input and providing improved visual feedback both reduce power usage and improve battery life of the system by enabling the user to use the device more quickly and efficiently.

In some embodiments, the representation (e.g., 814A) of the noise level at the plurality of different times includes an indication (e.g., 812E of FIG. 8D) of the maximum environmental noise level detected during the plurality of different times. Providing an indication of the maximum detected noise level during a period of interest provides a user with feedback as to sounds detected during that period. Providing improved visual feedback reduces power usage and improves battery life of the system by enabling the user to use the device more quickly and efficiently.

In some embodiments, the representation (e.g., 814B) of the noise level at the plurality of different times includes an indication of the maximum noise level detected during the plurality of different times, as reduced by sound reduction effects during the plurality of different times. Providing an indication of the maximum detected and reduced noise level during a period of interest provides a user with feedback as to sounds detected during that period and sound reduction effects during that period. Providing improved visual feedback reduces power usage and improves battery life of the system by enabling the user to use the device more quickly and efficiently.

In some embodiments, the representation of the noise level at the plurality of different times includes an indication (e.g., 812C) of an average noise level (e.g., an average environmental noise level and/or an average noise level with sound reduction) during the plurality of different times. Providing an indication of the average noise level during a period of interest provides a user with feedback as to sounds detected during that period. Providing improved visual feedback reduces power usage and improves battery life of the system by enabling the user to use the device more quickly and efficiently.

In some embodiments, the representation of the noise level at the plurality of different times includes an indication (e.g., 812F) of one or more sound-related notifications (e.g., notifications pertaining to environmental and/or reduced-level sound) (a number of such notifications, a summary of such notifications) that were issued (e.g., issued by the computer system or other computer systems associated with the user) during the plurality of different times. Providing an indication of sound-related notifications for a period provides a user with feedback as to such notifications that were issued during that period. Providing improved visual feedback reduces power usage and improves battery life of the system by enabling the user to use the device more quickly and efficiently.

In some embodiments, the representation of the noise level at the plurality of different times includes an indication (e.g., 812E) of a range of noise levels (e.g., range of environmental and/or reduced levels; a minimum and a maximum level) detected during the plurality of different times. Providing an indication of the range of noise levels during a period of interest provides a user with feedback as to sounds detected during that period. Providing improved visual feedback reduces power usage and improves battery life of the system by enabling the user to use the device more quickly and efficiently.

Note that details of the processes described above with respect to method 900 (e.g., FIGS. 9A-9B) are also applicable in an analogous manner to the methods described above/below. For example, methods 700 and 1000 optionally includes one or more of the characteristics of the various methods described above with reference to method 900. For example, the environmental sound level graph with a sound reduction option elements of method 900 and the sound reduction graph elements of method 1000 can be combined with the indication of a noise level a user is exposed to while using a sound reduction device or not using a sound reduction device elements of method 700 within one or more user interfaces of one or more of user devices 600B and 600C. For brevity, these details are not repeated below.

FIG. 10 is a flow diagram illustrating a method 1000 for managing and visualizing sound reduction, in accordance with some embodiments. Method 1000 is performed at a computer system (e.g., 100, 300, 500, 600B, 600C) (e.g., a smart watch, a smart phone, a personal computer, a laptop, a tablet) that is in communication with a display generation component (e.g., 602A, 602B) (e.g., an integrated display and/or a connected display). In some embodiments, the computer system is tablet, phone, laptop, desktop, a head mounted display ("HMD"), device with a mechanical wheelbase, self-propelled device, smart speaker, personal assistive device, robot, and/or camera. Some operations in method 1000 are, optionally, combined, the orders of some operations are, optionally, changed, and some operations are, optionally, omitted.

The computer system displays (1002), via the display generation component, a first representation (e.g., 814C) (e.g., a graph, a chart) of a sound reduction level (e.g., a sound reduction level based on a sound reduction effect (e.g., a passive or active effect)) (e.g., an amount of sound reduction by a sound reduction device (e.g., noise-canceling/noise mitigating headphones, passive earplugs, and/or active earplugs)) for a first time period (e.g., 810) corresponding to a first plurality of times, (e.g., times when a user of the computer system was using the sound reduction device at the two or more different times) wherein the first representation includes a first indication of a sound reduction level (e.g., a quantitative indication (e.g., a value in decibels of sound reduced)) (e.g., a first day (e.g., a Monday)) (e.g., the first time is one of the times of the first plurality of different times) at a first time of the first plurality of times (e.g., a day, a week, a month, a year) (e.g., different times in a given day, different days of the week, different weeks in a year), and a second indication (e.g., a quantitative indication (e.g., a value in decibels of sound reduced) of a sound reduction level at a second time of the first plurality of times that is different from the first time. In some embodiments, the indication is an indication of an instantaneous amount of sound reduction at the first time. In some embodiments, the first time is range of time (e.g., a day) and the indication is an indication of an average amount of sound reduction over that range of time). In some embodiments, the indication is an indication of an instantaneous amount of sound reduction at the second time. In some embodiments, the second time is range of time (e.g., a day) and the indication is an indication of an average amount of sound reduction over that range of time.

The computer system, while displaying the first representation, receives (1004), via the one or more input devices, a set of one or more inputs (804E, 804f) (e.g., enabled via user input on an affordance) corresponding to selection of a display option for a second time period (e.g., a day, a week, a month, a year) corresponding to a second plurality of times that is different from the first plurality of times. In some embodiments, the display option for the first time period option is an affordance that allows a user to select a specific time period, such as a day, a week, or a month. In some embodiments, the option is a selectable option that is separate from additional options/affordances for displaying different time periods.

The computer system, in response to receiving the set of one or more inputs, displays (1006), via the display generation component, a second representation (e.g., 814D, 814E) of a sound reduction level at the second plurality of times, wherein the second representation includes a third indication of a sound reduction level at a third time of the second plurality of times, a fourth indication of a sound reduction level at a fourth time of the second plurality of times that is different from the third time. In some embodiments, the third time and/or the fourth time is a subset of the first time (e.g., the first time is a week and the third time is a day within that week (e.g., the indications in the second representation of a sound reduction level are more granular than the indications in the first representation of a sound reduction level)). In some embodiments, the first time and/or the second time is a subset of the third time (e.g., the first time is a first day of the week and the second time is a second day of the week with the third time being the entire week).

In accordance with a determination that the display option (e.g., "D" as shown in FIGS. 8F-8H) for the second time period corresponds to a first display option (e.g., an option for a shorter time period than the currently displayed time period (e.g., the current time period is a week view and the requested time period is a day view)), the second time period is a subset of the first time period (e.g., the second time period a shorter time period than the first time period and falls within the first time period), in accordance with a determination that the display option for the second time period corresponds to a second display option (e.g., an option for a longer time period than the currently displayed time period (e.g., the current time period is a week view and the requested time period is a month view)), the first time period is a subset of the second time period (e.g., the second time period is a longer time period that includes the entirety of the first time period). Providing a user with options to view sound reduction data for different time periods, via a selectable option, provides the user with additional control options. Providing additional control of the system without cluttering the UI with additional displayed controls enhances the operability of the system and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system is in communication with one or more audio sensors (e.g., 606) (e.g., microphones), and the sound reduction level for the first time period is based on noise detected by the one or more audio sensors, and the sound reduction device is an external sound reduction device (e.g., 600A) (e.g., external noise-canceling/noise mitigating headphones, passive earplugs, and/or active earplugs). In some embodiments, the sound reduction level is a difference between noise detected by a first microphone and a noise detected by a second microphone. In some embodiments, the sound reduction level is calculated based on an environmental noise level measured by the one or more audio sensors).

In some embodiments, the one or more audio sensors are integrated into an external computer system (e.g., 600B) (e.g., a smart watch) that is in communication with the computer system, and the first representation of the sound reduction level for the first time period corresponding to a first plurality of times is included in a user interface (e.g., 802B) of a health application (e.g., 614) that generates (e.g., manages, includes) a plurality of user interfaces based on biometric data of a user of the computer system. In some embodiments, the second representation of the sound reduction level for the first time period corresponding to a first plurality of times is included in the user interface of the health application. Including first representation as part of a health application provides the user with feedback as to various biometric parameters relevant to the user's health. Providing improved visual feedback reduces power usage and improves battery life of the system by enabling the user to use the device more quickly and efficiently.

In some embodiments, in accordance with a determination that the sound reduction device provides a dynamic sound reduction effect (e.g., as shown in FIGS. 8F-8G at 814C and 814D), the first indication of a sound reduction level indicates a level of sound reduction that is different from the level of sound reduction indicated by the second indication of a sound reduction level (e.g., the sound reduction level is 10 decibels for the first time period and 5 decibels at the second time period). Automatically providing indications of different sound reduction levels at different times when the device is capable of providing a dynamic reduction effect automatically provides the user with a more accurate indication, when certain conditions are met. Performing an operation when a set of conditions has been met without requiring further user input and providing improved visual feedback both reduce power usage and improve battery life of the system by enabling the user to use the device more quickly and efficiently.

In some embodiments, in accordance with a determination that the sound reduction device provides a static sound reduction effect (e.g., as shown in FIG. 8H at 814E), the first indication of a sound reduction level and the second indication of sound reduction level indicate the same sound reduction level (e.g., the sound reduction level is 10 decibels for the first time period and 10 decibels at the second time period). Automatically providing indications of the same sound reduction level at different times when the device provides a static sound reduction effect automatically provides the user with an accurate indication, when certain conditions are met. Performing an operation when a set of conditions has been met without requiring further user input and providing improved visual feedback both reduce power usage and improve battery life of the system by enabling the user to use the device more quickly and efficiently.

In some embodiments, the first representation of the sound reduction level includes an indication (e.g., 818A, 818B, 818C) of a range (e.g., a minimum value and a maximum value (e.g., 10-30 decibels)) of sound reduction effect for the first time period. Providing an indication of a range of sound reduction for the first time period provides the user with improved feedback as the variations in sound reduction during the first time period. Providing improved visual feedback reduces power usage and improves battery life of the system by enabling the user to use the device more quickly and efficiently.

In some embodiments, the first representation of the sound reduction level includes an indication of a range (e.g., 818C) (e.g., a minimum value and a maximum value (e.g., 10-30 decibels)) of time during which a sound reduction effect was determined to in be in effect during the first time period (e.g., the first time period is the current day and a range of 8 AM to 11 AM is indicated for when the effect was active). Providing an indication of a range of time when the sound reduction effect was active during the first time period provides the user with improved feedback as to the timing of the effect. Providing improved visual feedback reduces power usage and improves battery life of the system by enabling the user to use the device more quickly and efficiently.

In some embodiments, the first indication of a sound reduction level is a numerical indication of a sound reduction level (e.g., as shown by 818C in FIG. 8H) (e.g., 10 decibels). Providing a numerical indication of a sound reduction effect provides the user with improved feedback as to magnitude of the effect. Providing improved visual feedback reduces power usage and improves battery life of the system by enabling the user to use the device more quickly and efficiently.

In some embodiments, prior to displaying the first representation of the sound reduction level for the first time period, displaying, via the display generation component, a summary user interface (e.g., 802B, 802C) of a health application (e.g., 614) (e.g., an application that presents data and/or functions relating to biometric data of the user of the computer system) that includes a first selectable user interface object (e.g., 808B) that corresponds to sound reduction data (e.g., data used to generate the first representation of the sound reduction level at the first time period), and a second selectable user interface object (e.g., a summary of noise/sound related data) that corresponds to a biometric parameter other than sound (e.g., heart rate, sleep, physical activity, menstrual cycle) that, when selected, initiates a process for displaying a user interface corresponding to the biometric parameter other than sound. Prior to displaying the first representation of the sound reduction level for the first time period, receiving, via the one or more input devices, a second set of one or more inputs (e.g., 804D) (e.g., taps, swipes, key presses, and/or mouse clicks) that includes an input corresponding to the first selectable user interface object that corresponds to sound reduction, wherein the first representation of the sound reduction level for the first time period is displayed in response to the second set of one or more inputs. Providing the first representation as part of a health application that includes user interfaces for other biometric parameters provides the user with options for viewing other health-related data via separate user interfaces. Providing additional control of the system without cluttering the UI with additional displayed controls enhances the operability of the system and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first time, the second time, the third time, and the fourth time are equal lengths of time (e.g., as shown in FIG. 8F-8H)(e.g., all represent an hour, or all represent a day).

In some embodiments, in accordance with a determination that the display option for the second time period corresponds to a first display option (e.g., as shown in FIG. 8F), with the second time period being a subset of the first time period, the third time is a shorter time period than the first time period (e.g., the first time period is a day and the third time period is an hour), and in accordance with a determination that the display option for the second time period corresponds to a second display option, with the first time period being a subset of the second time period (e.g., as shown in FIG. 8G), the third time is a longer time period than the first time period (e.g., the first time period is a week and the second time period is a month). Adjusting the period of time represented by the indications (e.g., the third indication) automatically based on the selected option provides the user with different detail levels as the plurality of times (e.g., the time range) changes and feedback as to the relationship between the selected time ranges. Performing an operation when a set of conditions has been met without requiring further user input and providing improved visual feedback both reduce power usage and improve battery life of the system by enabling the user to use the device more quickly and efficiently.

Note that details of the processes described above with respect to method 1000 (e.g., FIG. 10) are also applicable in an analogous manner to the methods described above. For example, methods 700 and 900 optionally includes one or more of the characteristics of the various methods described above with reference to method 1000. For example, the environmental sound level graph with a sound reduction option elements of method 900 and the sound reduction graph elements of method 1000 can be combined with the indication of a noise level a user is exposed to while using a sound reduction device or not using a sound reduction device elements of method 700 within one or more user interfaces of one or more of user devices 600B and 600C. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery of data, such as sound-related data. The present disclosure contemplates that in some instances, this gathered data may include personal information data that uniquely identifies or can be used to contact or locate a specific person. Such personal information data can include demographic data, location-based data, telephone numbers, email addresses, social network IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to better provide sound-related data. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of managing and visualizing sound reduction, the present technology can be configured to allow users to select to "opt in" or "opt out" of participation in the collection of personal information data during registration for services or anytime thereafter. In another example, users can select not to provide sound reduction-associated data for targeted managing and visualizing sound reduction. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, managing and visualizing sound reduction information can be made available to users by inferring preferences based on non-personal information data or a bare minimum amount of personal information, such as the content being requested by the device associated with a user, other non-personal information available to the managing and visualizing sound reduction applications, or publicly available information.

What is claimed is:

1. A computer system that is configured to communicate with a display generation component, the computer system comprising:
   one or more processors; and
   memory storing one or more programs configured to be executed by the one or more processors, the one or more programs including instructions for:
   displaying, via the display generation component, a representation of a noise level at a plurality of different times, wherein the representation includes:
   in accordance with a determination that a sound reduction display option is enabled:
   a first indication of a noise level at a first time of the plurality of different times that indicates:
   in accordance with a determination that sound reduction was in effect at the first time, a first noise level, wherein the first noise level is based on an environmental noise level at the first time and a first sound reduction effect that was in effect at the first time; and
   in accordance with a determination that sound reduction was not in effect at the first time, a second noise level that is greater than the first noise level, wherein the second noise level is based on the environmental noise level at the first time;
   a second indication of a noise level at a second time of the plurality of different times that is different from the first time and that indicates:
   in accordance with a determination that sound reduction was in effect at the second time, a third noise level, wherein the third noise level is based on an environmental noise level at the second time and a second sound reduction effect that was in effect at the second time; and
   in accordance with a determination that sound reduction was not in effect at the second time, a fourth noise level that is greater than the third noise level, wherein the fourth noise level is based on the environmental noise level at the second time;
   in accordance with a determination that the sound reduction display option is not enabled:
   a third indication of a noise level at the first time that indicates the second noise level; and
   a fourth indication of a noise level at the second time that indicates the fourth noise level.

2. The computer system of claim 1, the one or more programs further including instructions for:

while the sound reduction display option is not enabled, receiving a first user input corresponding to a request to enable the sound reduction display option; and in response to receiving the first user input, updating the representation of the noise level at the plurality of different times to include the first indication of the noise level at the first time and the second indication of the noise level at the second time.

3. The computer system of claim 1, the one or more programs further including instructions for:

while the sound reduction display option is enabled, receiving a second user input corresponding to a request to disable the sound reduction display option; and in response to receiving the second user input, updating the representation of the noise level at the plurality of different times to include the third indication of the noise level at the first time and the fourth indication of the noise level at the second time.

4. The computer system of claim 1, wherein:

the computer system is in communication with one or more audio sensors;

the noise level at the plurality of different times are detected via the one or more audio sensors; and a sound reduction device is an external sound reduction device.

5. The computer system of claim 4, wherein:

the one or more audio sensors are integrated into an external computer system that is in communication with the computer system; and the representation of the noise level at the plurality of different times is included in a user interface of a health application that generates a plurality of user interfaces based on biometric data of a user of the computer system.

6. The computer system of claim 1, wherein:

while the sound reduction display option is not enabled:

the third indication is a graphical indication that varies along a first axis to indicate a range of environmental noise levels at the first time;

the fourth indication is a graphical indication that varies along the first axis to indicate a range of environmental noise levels at the second time;

the third indication and fourth indication are arranged along a second axis, different from the first axis; and the representation of the noise level at the plurality of different times includes a first average noise level indication that extends along the second axis and that indicates an average environmental noise level during the plurality of different times.

7. The computer system of claim 1, wherein:

while the sound reduction display option is enabled:

the first indication is a graphical indication and includes a first subportion that varies along a third axis and indicates a range of the noise level at the first time, as reduced by the first sound reduction effect at the first time;

the second indication is a graphical indication that includes a second subportion that varies along the third axis and indicates a range of the noise level at the second time, as reduced by the second sound reduction effect at the second time;

the first indication and second indication are arranged along a fourth axis, different from the third axis; and the representation of the noise level at the plurality of different times includes a second average noise level indication that extends along the fourth axis and that indicates an average noise level during the plurality of different times, as reduced by the first sound reduction effect during the plurality of different times.

8. The computer system of claim 7, wherein:

the first indication includes a third subportion that varies along the third axis and indicates a range of environmental noise levels at the first time;

the second indication includes a fourth subportion that varies along the third axis and indicates a range of environmental noise levels at the second time; and the representation of the noise level at the plurality of different times includes a third average noise level indication that extends along the fourth axis and that indicates an average environmental noise level during the plurality of different times.

9. The computer system of claim 1, wherein the determination that sound reduction was in effect at the first time includes a determination that a user of the computer system was wearing a sound reduction device for both ears.

10. The computer system of claim 1, wherein the representation of the noise level at the plurality of different times includes an indication of a maximum environmental noise level detected during the plurality of different times.

11. The computer system of claim 1, wherein the representation of the noise level at the plurality of different times includes an indication of a maximum noise level detected during the plurality of different times, as reduced by sound reduction effects during the plurality of different times.

12. The computer system of claim 1, wherein the representation of the noise level at the plurality of different times includes an indication of an average noise level during the plurality of different times.

13. The computer system of claim 1, wherein the representation of the noise level at the plurality of different times includes an indication of one or more sound-related notifications that were issued during the plurality of different times.

14. The computer system of claim 1, wherein the representation of the noise level at the plurality of different times includes an indication of a range of noise levels detected during the plurality of different times.

15. A non-transitory computer-readable storage medium storing one or more programs configured to be executed by one or more processors of a computer system that is in communication with a display generation component, the one or more programs including instructions for:

displaying, via the display generation component, a representation of a noise level at a plurality of different times, wherein the representation includes:

in accordance with a determination that a sound reduction display option is enabled:

a first indication of a noise level at a first time of the plurality of different times that indicates:

in accordance with a determination that sound reduction was in effect at the first time, a first noise level, wherein the first noise level is based on an environmental noise level at the first time and a first sound reduction effect that was in effect at the first time; and in accordance with a determination that sound reduction was not in effect at the first time, a second noise level that is greater than the first noise level, wherein the second noise level is based on the environmental noise level at the first time;

a second indication of a noise level at a second time of the plurality of different times that is different from the first time and that indicates:
in accordance with a determination that sound reduction was in effect at the second time, a third noise level, wherein the third noise level is based on an environmental noise level at the second time and a second sound reduction effect that was in effect at the second time; and
in accordance with a determination that sound reduction was not in effect at the second time, a fourth noise level that is greater than the third noise level, wherein the fourth noise level is based on the environmental noise level at the second time;
in accordance with a determination that the sound reduction display option is not enabled:
a third indication of a noise level at the first time that indicates the second noise level; and
a fourth indication of a noise level at the second time that indicates the fourth noise level.

16. A method comprising:
at a computer system that is in communication with a display generation component:
displaying, via the display generation component, a representation of a noise level at a plurality of different times, wherein the representation includes:
in accordance with a determination that a sound reduction display option is enabled:
a first indication of a noise level at a first time of the plurality of different times that indicates:
in accordance with a determination that sound reduction was in effect at the first time, a first noise level, wherein the first noise level is based on an environmental noise level at the first time and a first sound reduction effect that was in effect at the first time; and
in accordance with a determination that sound reduction was not in effect at the first time, a second noise level that is greater than the first noise level, wherein the second noise level is based on the environmental noise level at the first time;
a second indication of a noise level at a second time of the plurality of different times that is different from the first time and that indicates:
in accordance with a determination that sound reduction was in effect at the second time, a third noise level, wherein the third noise level is based on an environmental noise level at the second time and a second sound reduction effect that was in effect at the second time; and
in accordance with a determination that sound reduction was not in effect at the second time, a fourth noise level that is greater than the third noise level, wherein the fourth noise level is based on the environmental noise level at the second time;
in accordance with a determination that the sound reduction display option is not enabled:
a third indication of a noise level at the first time that indicates the second noise level; and
a fourth indication of a noise level at the second time that indicates the fourth noise level.

17. The non-transitory computer-readable storage medium of claim 15, the one or more programs further including instructions for:
while the sound reduction display option is not enabled, receiving a first user input corresponding to a request to enable the sound reduction display option; and
in response to receiving the first user input, updating the representation of the noise level at the plurality of different times to include the first indication of the noise level at the first time and the second indication of the noise level at the second time.

18. The non-transitory computer-readable storage medium of claim 15, the one or more programs further including instructions for:
while the sound reduction display option is enabled, receiving a second user input corresponding to a request to disable the sound reduction display option; and
in response to receiving the second user input, updating the representation of the noise level at the plurality of different times to include the third indication of the noise level at the first time and the fourth indication of the noise level at the second time.

19. The non-transitory computer-readable storage medium of claim 15, wherein:
the computer system is in communication with one or more audio sensors;
the noise level at the plurality of different times are detected via the one or more audio sensors; and
a sound reduction device is an external sound reduction device.

20. The non-transitory computer-readable storage medium of claim 19, wherein:
the one or more audio sensors are integrated into an external computer system that is in communication with the computer system; and
the representation of the noise level at the plurality of different times is included in a user interface of a health application that generates a plurality of user interfaces based on biometric data of a user of the computer system.

21. The non-transitory computer-readable storage medium of claim 15, wherein:
while the sound reduction display option is not enabled:
the third indication is a graphical indication that varies along a first axis to indicate a range of environmental noise levels at the first time;
the fourth indication is a graphical indication that varies along the first axis to indicate a range of environmental noise levels at the second time;
the third indication and fourth indication are arranged along a second axis, different from the first axis; and
the representation of the noise level at the plurality of different times includes a first average noise level indication that extends along the second axis and that indicates an average environmental noise level during the plurality of different times.

22. The non-transitory computer-readable storage medium of claim 15, wherein:
while the sound reduction display option is enabled:
the first indication is a graphical indication and includes a first subportion that varies along a third axis and indicates a range of the noise level at the first time, as reduced by the first sound reduction effect at the first time;
the second indication is a graphical indication that includes a second subportion that varies along the third axis and indicates a range of the noise level at the second time, as reduced by the second sound reduction effect at the second time;

the first indication and second indication are arranged along a fourth axis, different from the third axis; and the representation of the noise level at the plurality of different times includes a second average noise level indication that extends along the fourth axis and that indicates an average noise level during the plurality of different times, as reduced by the first sound reduction effect during the plurality of different times.

23. The non-transitory computer-readable storage medium of claim 22, wherein:

the first indication includes a third subportion that varies along the third axis and indicates a range of environmental noise levels at the first time;

the second indication includes a fourth subportion that varies along the third axis and indicates a range of environmental noise levels at the second time; and the representation of the noise level at the plurality of different times includes a third average noise level indication that extends along the fourth axis and that indicates an average environmental noise level during the plurality of different times.

24. The non-transitory computer-readable storage medium of claim 15, wherein the determination that sound reduction was in effect at the first time includes a determination that a user of the computer system was wearing a sound reduction device for both ears.

25. The non-transitory computer-readable storage medium of claim 15, wherein the representation of the noise level at the plurality of different times includes an indication of a maximum environmental noise level detected during the plurality of different times.

26. The non-transitory computer-readable storage medium of claim 15, wherein the representation of the noise level at the plurality of different times includes an indication of a maximum noise level detected during the plurality of different times, as reduced by sound reduction effects during the plurality of different times.

27. The non-transitory computer-readable storage medium of claim 15, wherein the representation of the noise level at the plurality of different times includes an indication of an average noise level during the plurality of different times.

28. The non-transitory computer-readable storage medium of claim 15, wherein the representation of the noise level at the plurality of different times includes an indication of one or more sound-related notifications that were issued during the plurality of different times.

29. The non-transitory computer-readable storage medium of claim 15, wherein the representation of the noise level at the plurality of different times includes an indication of a range of noise levels detected during the plurality of different times.

30. The method of claim 16, further comprising:

while the sound reduction display option is not enabled, receiving a first user input corresponding to a request to enable the sound reduction display option; and in response to receiving the first user input, updating the representation of the noise level at the plurality of different times to include the first indication of the noise level at the first time and the second indication of the noise level at the second time.

31. The method of claim 16, further comprising:

while the sound reduction display option is enabled, receiving a second user input corresponding to a request to disable the sound reduction display option; and in response to receiving the second user input, updating the representation of the noise level at the plurality of different times to include the third indication of the noise level at the first time and the fourth indication of the noise level at the second time.

32. The method of claim 16, wherein:

the computer system is in communication with one or more audio sensors;

the noise level at the plurality of different times are detected via the one or more audio sensors; and a sound reduction device is an external sound reduction device.

33. The method of claim 32, wherein:

the one or more audio sensors are integrated into an external computer system that is in communication with the computer system; and the representation of the noise level at the plurality of different times is included in a user interface of a health application that generates a plurality of user interfaces based on biometric data of a user of the computer system.

34. The method of claim 16, wherein:

while the sound reduction display option is not enabled:

the third indication is a graphical indication that varies along a first axis to indicate a range of environmental noise levels at the first time;

the fourth indication is a graphical indication that varies along the first axis to indicate a range of environmental noise levels at the second time;

the third indication and fourth indication are arranged along a second axis, different from the first axis; and the representation of the noise level at the plurality of different times includes a first average noise level indication that extends along the second axis and that indicates an average environmental noise level during the plurality of different times.

35. The method of claim 16, wherein:

while the sound reduction display option is enabled:

the first indication is a graphical indication and includes a first subportion that varies along a third axis and indicates a range of the noise level at the first time, as reduced by the first sound reduction effect at the first time;

the second indication is a graphical indication that includes a second subportion that varies along the third axis and indicates a range of the noise level at the second time, as reduced by the second sound reduction effect at the second time;

the first indication and second indication are arranged along a fourth axis, different from the third axis; and the representation of the noise level at the plurality of different times includes a second average noise level indication that extends along the fourth axis and that indicates an average noise level during the plurality of different times, as reduced by the first sound reduction effect during the plurality of different times.

36. The method of claim 35, wherein:

the first indication includes a third subportion that varies along the third axis and indicates a range of environmental noise levels at the first time;

the second indication includes a fourth subportion that varies along the third axis and indicates a range of environmental noise levels at the second time; and the representation of the noise level at the plurality of different times includes a third average noise level indication that extends along the fourth axis and that indicates an average environmental noise level during the plurality of different times.

37. The method of claim 16, wherein the determination that sound reduction was in effect at the first time includes a determination that a user of the computer system was wearing a sound reduction device for both ears.

38. The method of claim 16, wherein the representation of the noise level at the plurality of different times includes an indication of a maximum environmental noise level detected during the plurality of different times.

39. The method of claim 16, wherein the representation of the noise level at the plurality of different times includes an indication of a maximum noise level detected during the plurality of different times, as reduced by sound reduction effects during the plurality of different times.

40. The method of claim 16, wherein the representation of the noise level at the plurality of different times includes an indication of an average noise level during the plurality of different times.

41. The method of claim 16, wherein the representation of the noise level at the plurality of different times includes an indication of one or more sound-related notifications that were issued during the plurality of different times.

42. The method of claim 16, wherein the representation of the noise level at the plurality of different times includes an indication of a range of noise levels detected during the plurality of different times.

\* \* \* \* \*